(12) United States Patent
Scola et al.

(10) Patent No.: US 7,935,670 B2
(45) Date of Patent: May 3, 2011

(54) HEPATITIS C VIRUS INHIBITORS

(75) Inventors: Paul Michael Scola, Glastonbury, CT (US); Li-Qiang Sun, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 207 days.

(21) Appl. No.: 11/775,341

(22) Filed: Jul. 10, 2007

(65) Prior Publication Data

US 2008/0014173 A1 Jan. 17, 2008

Related U.S. Application Data

(60) Provisional application No. 60/819,903, filed on Jul. 11, 2006.

(51) Int. Cl.
*A61K 38/00* (2006.01)
(52) U.S. Cl. ........................................................ 514/4.1
(58) Field of Classification Search ........................ None
See application file for complete search history.

(56) References Cited

U.S. PATENT DOCUMENTS

| | | | |
|---|---|---|---|
| 5,223,432 | A | 6/1993 | Wirz et al. |
| 7,041,698 | B2 * | 5/2006 | Ripka et al. ................... 514/423 |
| 2005/0153877 | A1 | 7/2005 | Miao et al. |
| 2006/0172950 | A1 | 8/2006 | Wang et al. |
| 2006/0199773 | A1 | 9/2006 | Sausker et al. |
| 2006/0257980 | A1 | 11/2006 | Li |
| 2007/0078081 | A1 | 4/2007 | Casarez et al. |

FOREIGN PATENT DOCUMENTS

| | | |
|---|---|---|
| WO | WO 98/17679 | 4/1998 |
| WO | WO 99/07733 | 2/1999 |
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 02/08244 | 1/2002 |
| WO | WO 02/060926 | 8/2002 |
| WO | WO 03/053349 | 7/2003 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 03/099274 | 12/2003 |
| WO | WO 03/099316 | 12/2003 |
| WO | WO 2004/009121 | 1/2004 |
| WO | WO 2004/032827 | 4/2004 |
| WO | WO 2004/037855 | 5/2004 |
| WO | WO 2004/043339 | 5/2004 |
| WO | WO 2004/072243 | 8/2004 |
| WO | WO 2004/093798 | 11/2004 |
| WO | WO 2004/093915 | 11/2004 |
| WO | WO 2004/094452 | 11/2004 |
| WO | WO 2004/101602 | 11/2004 |
| WO | WO 2004/101605 | 11/2004 |
| WO | WO 2004/103996 | 12/2004 |
| WO | WO 2004/113365 | 12/2004 |
| WO | WO 2005/010029 | 2/2005 |
| WO | WO 2005/028501 | 3/2005 |
| WO | WO 2005/037214 | 4/2005 |
| WO | WO 2005/037860 | 4/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/070955 | 8/2005 |
| WO | WO 2005/073216 | 8/2005 |
| WO | WO 2005/095403 | 10/2005 |
| WO | WO 2005/116054 | 12/2005 |
| WO | WO 2006/000085 | 1/2006 |
| WO | WO 2006/007700 | 1/2006 |
| WO | WO 2006/007708 | 1/2006 |
| WO | WO 2006/016930 | 2/2006 |
| WO | WO 2006/020276 | 2/2006 |
| WO | WO 2006/026352 | 3/2006 |
| WO | WO 2006/033878 | 3/2006 |
| WO | WO 2006/043145 | 4/2006 |
| WO | WO 2006/086381 | 8/2006 |
| WO | WO 2006/096652 | 9/2006 |
| WO | WO 2006/119061 | 11/2006 |
| WO | WO 2006/122188 | 11/2006 |
| WO | WO 2006/130552 | 12/2006 |
| WO | WO 2006/130553 | 12/2006 |
| WO | WO 2006/130554 | 12/2006 |
| WO | WO 2006/130607 | 12/2006 |
| WO | WO 2006/130626 | 12/2006 |
| WO | WO 2006/130627 | 12/2006 |
| WO | WO 2006/130628 | 12/2006 |
| WO | WO 2006/130666 | 12/2006 |
| WO | WO 2006/130686 | 12/2006 |
| WO | WO 2006/130688 | 12/2006 |

(Continued)

OTHER PUBLICATIONS

Lauer G. M. et al., "Hepatitis C Virus Infection," New England Journal of Medicine, vol. 345 No. 1, pp. 41-52, (2001).

(Continued)

*Primary Examiner* — Cecilia Tsang
*Assistant Examiner* — Thomas S Heard
(74) *Attorney, Agent, or Firm* — Pamela A. Mingo

(57) ABSTRACT

Hepatitis C virus inhibitors having the general formula

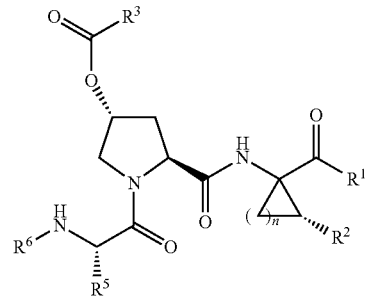

are disclosed. Compositions comprising the compounds and methods for using the compounds to inhibit HCV are also disclosed.

20 Claims, No Drawings

FOREIGN PATENT DOCUMENTS

| | | |
|---|---|---|
| WO | WO 2007/001406 | 1/2007 |
| WO | WO 2007/008657 | 1/2007 |
| WO | WO 2007/009109 | 1/2007 |
| WO | WO 2007/009227 | 1/2007 |
| WO | WO 2007/014918 | 2/2007 |
| WO | WO 2007/014919 | 2/2007 |
| WO | WO 2007/014920 | 2/2007 |
| WO | WO 2007/014921 | 2/2007 |
| WO | WO 2007/014922 | 2/2007 |
| WO | WO 2007/014923 | 2/2007 |
| WO | WO 2007/014924 | 2/2007 |
| WO | WO 2007/014925 | 2/2007 |
| WO | WO 2007/014926 | 2/2007 |
| WO | WO 2007/014927 | 2/2007 |
| WO | WO 2007/015787 | 2/2007 |
| WO | WO 2007/015824 | 2/2007 |
| WO | WO 2007/015855 | 2/2007 |
| WO | WO 2007/016441 | 2/2007 |
| WO | WO 2007/016476 | 2/2007 |
| WO | WO 2007/017144 | 2/2007 |
| WO | WO 2007/025307 | 3/2007 |
| WO | WO 2007/044893 | 4/2007 |
| WO | WO 2007/044933 | 4/2007 |
| WO | WO 2007/056120 | 5/2007 |
| WO | WO 2007/082131 | 7/2007 |
| WO | WO 2006/130687 | 12/2008 |

OTHER PUBLICATIONS

Poupart, M.-A. et al., "Solid-Phase Synthesis of Peptidomimetic Inhibitors for the Hepatitis C Virus NS3 Protease," The Journal of Organic Chemistry, vol. 66 No. 14, pp. 4743-4751, (2001).

Yang, S., Hayden, W., Faber, K., Griengl, H., "Chemoenzymatic synthesis of (R)-(-)-citramalic acid", *Synthesis*, 1992, No. 4, 365-366 (process).

Wirz, B., and Soukup, M., "Enzymatic preparation of homochiral 2-isobutyl succinic acid derivatives", *Tetrahedron: Asymmetry*, 1997, 8, 187-189. (process).

Ribeiro, C.M.R., Passaroto, E.N., Brenelli, E.C.S., "Ultrasound in enzymatic resolution of ethyl 3-hydroxy-3-phenylpropanoate", *Tetrahedron Lett.*, 2001, 42, 6477-6479. (process).

Llinas-Brunet et al. (2004) Journal of Medicinal Chemistry, vol. 47 pp. 6584-6594 (acyclics).

\* cited by examiner

HEPATITIS C VIRUS INHIBITORS

CROSS-REFERENCE TO RELATED APPLICATIONS

This application claims the benefit of U.S. Provisional Application Ser. No. 60/819,903 filed Jul. 11, 2006.

The present disclosure is generally directed to antiviral compounds, and more specifically directed to compounds which inhibit the function of the NS3 protease (also referred to herein as "serine protease") encoded by Hepatitis C virus (HCV), compositions comprising such compounds, and methods for inhibiting the function of the NS3 protease.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. Six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one cleaves at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A is essential for efficient polyprotein processing, enhancing the proteolytic cleavage at all of the sites. The NS3 protein also exhibits nucleoside triphosphatase and RNA helicase activities. NS5B is a RNA-dependent RNA polymerase that is involved in the replication of HCV.

The present disclosure provides peptide compounds that can inhibit the functioning of the NS3 protease, e.g., in combination with the NS4A protease. Further, the present disclosure describes the administration of combination therapy to a patient whereby a compound in accordance with the present disclosure, which is effective to inhibit the HCV NS3 protease, can be administered with another compound having anti-HCV activity, e.g., a compound which is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

The first aspect of the present disclosure provides a compound of formula (I)

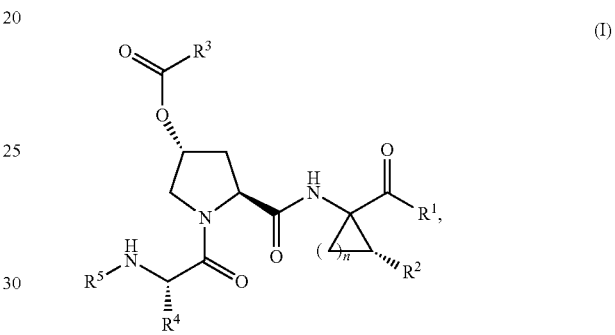

(I)

Or a pharmaceutically acceptable salt thereof, wherein
n is 1, 2, or 3;
$R^1$ is selected from hydroxy and —$NHSO_2R^6$;
$R^2$ is selected from hydrogen, alkenyl, alkyl, and cycloalkyl, wherein the alkenyl, the alkyl, and the cycloalkyl are optionally substituted with one, two, or three substituents independently selected from alkoxy, carboxy, cyano, dialkylamino, and halo;
$R^3$ is selected from alkenyl, alkoxy, alkyl, aryl, arylalkyl, aryloxy, cyanoalkyl, cycloalkyl, (cycloalkyl)alkyl, cycloalkyloxy, haloalkyl, heterocyclyl, heterocyclylalkyl, heterocyclyloxy, —$NR^aR^b$, and —$NR^cR^d$;
$R^4$ is selected from hydrogen, alkenyl, alkoxyalkyl, alkoxycarbonylalkyl, alkyl, arylalkyl, carboxyalkyl, cyanoalkyl, cycloalkyl, (cycloalkyl)alkyl, haloalkoxyalkyl, haloalkyl, heterocyclyl, hydroxyalkyl, ($NR^aR^b$)alkyl, and ($NR^cR^d$)alkyl;
$R^5$ is selected from hydrogen, alkoxycarbonyl, alkyl, alkylcarbonyl, alkylsulfonyl, aryloxycarbonyl, cycloalkyl, cycloalkyloxycarbonyl, haloalkoxycarbonyl, heterocyclyloxycarbonyl, ($NR^aR^b$)carbonyl, ($NR^aR^b$)sulfonyl, ($NR^cR^d$)carbonyl, and ($NR^cR^d$)sulfonyl;
$R^6$ is selected from alkyl, aryl, cycloalkyl, (cycloalkyl)alkyl, heterocyclyl, —$NR^aR^b$, and —$NR^cR^d$; wherein the cycloalkyl and the cycloalkyl part of the (cycloalkyl)alkyl can be optionally substituted with one substituent selected from alkoxy, alkyl, amino, cyano, halo, haloalkyl, and nitro;
$R^a$ and $R^b$ are independently selected from hydrogen, alkenyl, alkoxyalkyl, alkyl, aryl, arylalkyl, cycloalkyl, (cycloalkyl)alkyl, heterocyclyl, and heterocyclylalkyl; and
$R^c$ and $R^d$ together with the nitrogen atom to which they are attached form a five or six-membered monocyclic heterocyclic ring optionally containing one additional heteroatom selected from NH, O, and S;

provided that when R³ is either —NRᵃRᵇ or —NRᶜRᵈ then R⁶ is —NRᵃRᵇ.

In one embodiment of the first aspect the present disclosure R¹ is —NHSO₂R⁶.

The second aspect of the present disclosure provides a compound of formula (II)

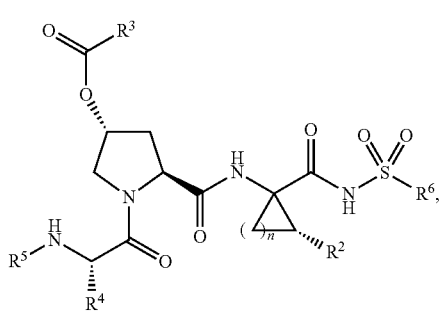

(II)

or a pharmaceutically acceptable salt thereof, wherein
n is 1, 2, or 3;
R² is selected from hydrogen, alkenyl, alkyl, and cycloalkyl, wherein the alkenyl, the alkyl, and the cycloalkyl are optionally substituted with one, two, or three substituents independently selected from alkoxy, carboxy, cyano, dialkylamino, and halo;
R³ is selected from alkyl, haloalkyl, cyanoalkyl, alkenyl, aryl, arylalkyl, cycloalkyl, (cycloalkyl)alkyl, heterocyclyl, and heterocyclylalkyl;
R⁴ is selected from hydrogen, alkenyl, alkyl, and haloalkyl;
R⁵ is selected from alkoxycarbonyl, alkylcarbonyl, (NRᵃRᵇ)carbonyl, and (NRᶜRᵈ)carbonyl;
R⁶ is selected from alkyl, aryl, cycloalkyl, (cycloalkyl)alkyl, heterocyclyl, —NRᵃRᵇ, and —NRᶜRᵈ; wherein the cycloalkyl and the cycloalkyl part of the (cycloalkyl)alkyl can be optionally substituted with one substituent selected from alkoxy, alkyl, amino, cyano, halo, haloalkyl, and nitro;
Rᵃ and Rᵇ are independently selected from hydrogen and alkyl; and
Rᶜ and Rᵈ together with the nitrogen atom to which they are attached form a five or six-membered monocyclic heterocyclic ring optionally containing one additional heteroatom selected from NH, O, and S.

In a first embodiment of the second aspect n is 1 or 2; and R⁴ is selected from hydrogen, alkenyl, and alkyl.

In a third embodiment of the second aspect n is 1; R² is alkenyl; R⁴ is alkyl; and R⁵ is alkoxycarbonyl.

The third aspect of the present disclosure provides a compound of formula (III)

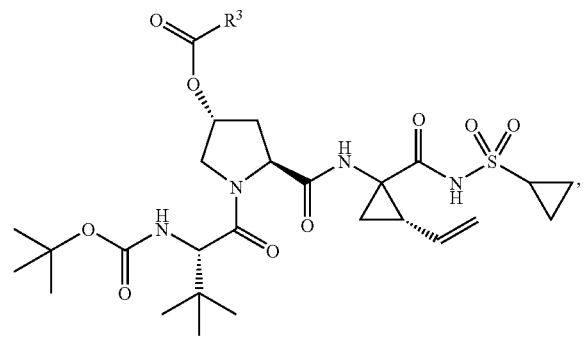

(III)

or a pharmaceutically acceptable salt thereof, wherein

R³ is selected from alkyl, haloalkyl, cyanoalkyl, alkenyl, aryl, arylalkyl, cycloalkyl, (cycloalkyl)alkyl, heterocyclyl, and heterocyclylalkyl.

In a first embodiment of the third aspect R³ is selected from aryl and heterocyclyl.

In a second embodiment of the third aspect R³ is selected from phenyl optionally substituted with one substituent selected from alkoxy, unsubstituted phenyl, and halo; and quinolinyl.

The fourth aspect of the present disclosure provides a compound selected from

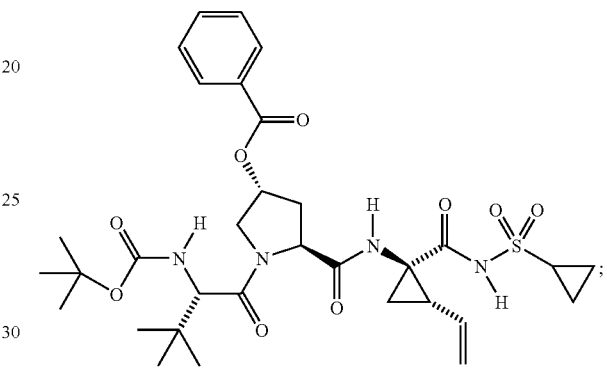

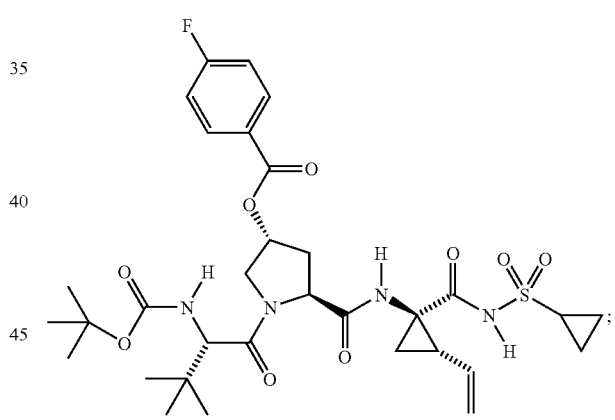

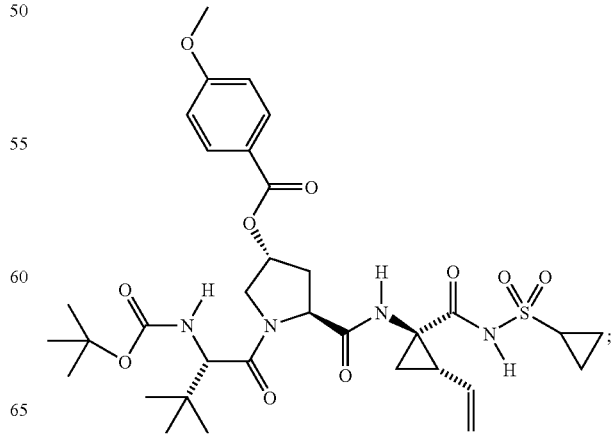

-continued

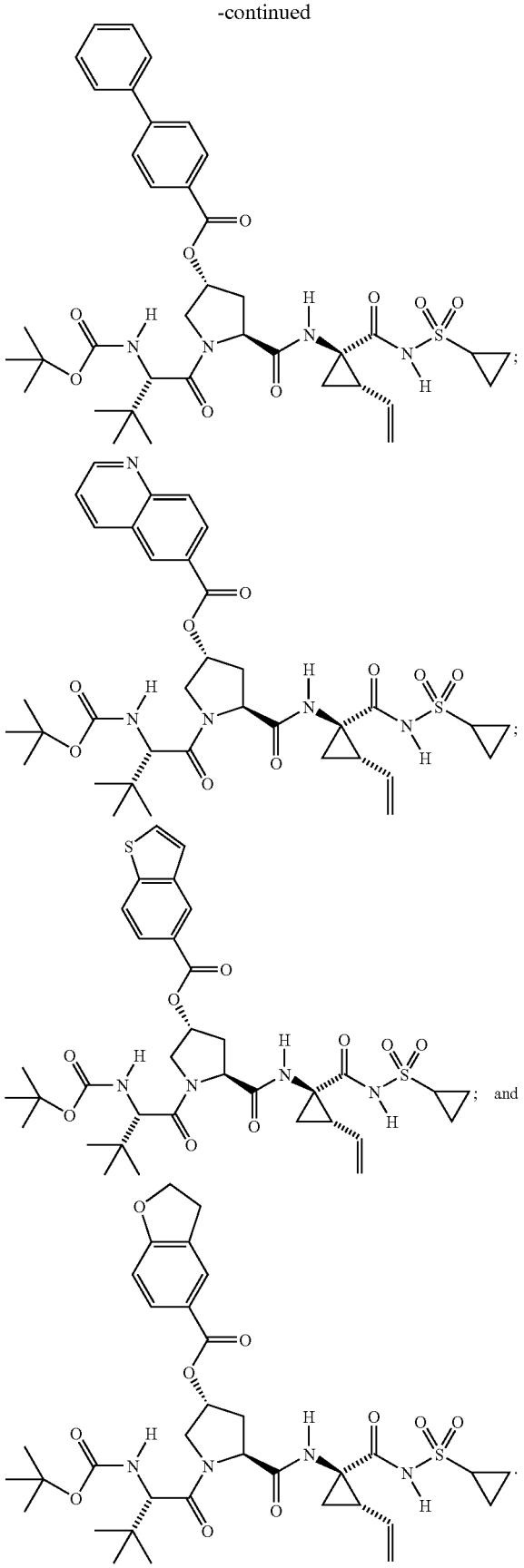

The fifth aspect of the present disclosure provides a composition comprising a compound of formula (I), and/or a pharmaceutically acceptable salt thereof, and a pharmaceutically acceptable carrier.

In a first embodiment of the fifth aspect the composition further comprises an interferon and ribavirin.

In a second embodiment of the fifth aspect the composition further comprises a second compound having anti-HCV activity.

In a third embodiment of the fifth aspect the composition further comprises a second compound having anti-HCV activity wherein the second compound having anti-HCV activity is an interferon.

In a fourth embodiment of the fifth aspect the composition further comprises a second compound having anti-HCV activity, wherein the second compound having anti-HCV activity is an interferon, wherein the interferon is selected from interferon alpha 2B, pegylated interferon alpha, consensus interferon, interferon alpha 2A, and lymphoblastiod interferon tau.

In a fifth embodiment of the fifth aspect the composition further comprises a second compound having anti-HCV activity, wherein the second compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

The sixth aspect of the present disclosure provides a method of inhibiting the function of HCV serine protease comprising contacting the HCV serine protease with a compound of formula (I), and/or a pharmaceutically acceptable salt thereof.

The seventh aspect of the present disclosure provides a method of treating an HCV infection in a patient, comprising administering to the patient a therapeutically effective amount of a compound of formula (I), and/or a pharmaceutically acceptable salt thereof.

In a first embodiment of the seventh aspect the compound of formula (I) is effective to inhibit the function of the HCV serine protease.

In a second embodiment of the seventh aspect the method further comprises administering a second compound having anti-HCV activity prior to, after, or simultaneously with the compound of formula (I), and/or a pharmaceutically acceptable salt thereof.

In a third embodiment of the seventh aspect the method further comprises administering a second compound having anti-HCV activity prior to, after, or simultaneously with the compound of formula (I), and/or a pharmaceutically acceptable salt thereof, wherein the second compound having anti-HCV activity is an interferon.

In a fourth embodiment of the seventh aspect the method further comprises administering a second compound having anti-HCV activity prior to, after, or simultaneously with the compound of formula (I), and/or a pharmaceutically acceptable salt thereof, wherein the second compound having anti-HCV activity is an interferon, wherein the interferon is selected from interferon alpha 2B, pegylated interferon alpha, consensus interferon, interferon alpha 2A, and lymphoblastiod interferon tau.

In a fifth embodiment of the seventh aspect the method further comprises administering a second compound having anti-HCV activity prior to, after, or simultaneously with the compound of formula (I), and/or a pharmaceutically acceptable salt thereof, wherein the second compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In another aspect the present disclosure provides a compound of formula (IV)

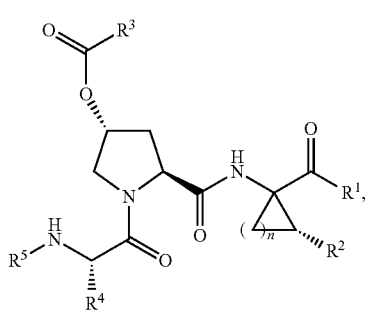

or a pharmaceutically acceptable salt thereof, wherein
n is 1, 2, or 3;
$R^1$ is selected from hydroxy and —NHSO$_2$R$^6$;
$R^2$ is selected from hydrogen, alkenyl, alkyl, and cycloalkyl, wherein the alkenyl, the alkyl, and the cycloalkyl are optionally substituted with one, two, or three substituents independently selected from alkoxy, carboxy, cyano, dialkylamino, and halo;
$R^3$ is selected from alkenyl, alkoxy, alkyl, aryl, arylalkyl, aryloxy, cyanoalkyl, cycloalkyl, (cycloalkyl)alkyl, cycloalkyloxy, haloalkyl, heterocyclyl, heterocyclylalkyl, heterocyclyloxy, —NR$^a$R$^b$, and —NR$^c$R$^d$;
$R^4$ is selected from hydrogen, alkenyl, alkoxyalkyl, alkoxycarbonylalkyl, alkyl, arylalkyl, carboxyalkyl, cyanoalkyl, cycloalkyl, (cycloalkyl)alkyl, haloalkoxyalkyl, haloalkyl, heterocyclyl, hydroxyalkyl, (NR$^a$R$^b$)alkyl, and (NR$^c$R$^d$)alkyl;
$R^5$ is selected from hydrogen, alkoxycarbonyl, alkyl, alkylcarbonyl, alkylsulfonyl, aryloxycarbonyl, cycloalkyl, cycloalkyloxycarbonyl, haloalkoxycarbonyl, heterocyclyloxycarbonyl, (NR$^a$R$^b$)carbonyl, (NR$^a$R$^b$)sulfonyl, (NR$^c$R$^d$)carbonyl, and (NR$^c$R$^d$)sulfonyl;
$R^6$ is selected from alkyl, aryl, cycloalkyl, (cycloalkyl)alkyl, heterocyclyl, —NR$^a$R$^b$, and —NR$^c$R$^d$; wherein the cycloalkyl and the cycloalkyl part of the (cycloalkyl)alkyl can be optionally substituted with one substituent selected from alkenyl, alkoxy, alkoxyalkyl, alkyl, amino, arylalkyl, arylcarbonyl, cyano, cycloalkenyl, a second cycloalkyl, a second (cycloalkyl)alkyl, halo, haloalkyl, nitro, and (NR'R")carbonyl; wherein the second cycloalkyl and the cycloalkyl part of the second (cycloalkyl)alkyl can be further optionally substituted with one hydroxy group; and wherein R' and R" are independently selected from hydrogen, alkyl, aryl, and heterocyclyl;
$R^a$ and $R^b$ are independently selected from hydrogen, alkenyl, alkoxyalkyl, alkyl, aryl, arylalkyl, cycloalkyl, (cycloalkyl)alkyl, heterocyclyl, and heterocyclylalkyl; and
$R^c$ and $R^d$ together with the nitrogen atom to which they are attached form a five or six-membered monocyclic heterocyclic ring optionally containing one additional heteroatom selected from NH, O, and S;
provided that when $R^3$ is either —NR$^a$R$^b$ or —NR$^c$R$^d$ then $R^6$ is —NR$^a$R$^b$.

Unless otherwise specifically noted herein, the terms set forth below will have the following definitions.

As used herein, the singular forms "a", "an", and "the" include plural reference unless the context clearly dictates otherwise.

The term "alkenyl," as used herein, refers to a straight or branched chain group of two to six carbon atoms containing at least one carbon-carbon double bond.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxycarbonyl," as used herein, refers to an alkoxy group attached to the parent molecular moiety through a carbonyl group.

The term "alkoxycarbonylalkyl," as used herein, refers to an alkyl group substituted with one, two, or three alkoxycarbonyl groups.

The term "alkyl," as used herein, refers to a group derived from a straight or branched chain saturated hydrocarbon containing from one to ten carbon atoms.

The term "alkylcarbonyl," as used herein, refers to an alkyl group attached to the parent molecular moiety through a carbonyl group.

The term "alkylsulfonyl," as used herein, refers to an alkyl group attached to the parent molecular moiety through a sulfonyl group.

The term "amino," as used herein, refers to —NH$_2$.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure can be optionally substituted with one, two, three, four, or five substituents independently selected from alkoxy, alkoxycarbonyl, alkyl, a second aryl group, cyano, halo, haloalkoxy, haloalkyl, heterocyclyl, heterocyclylalkyl, hydroxy, hydroxyalkyl, nitro, —NR$^x$R$^y$, (NR$^x$R$^y$)alkoxy, (NR$^x$R$^y$)alkyl, (NR$^x$R$^y$)carbonyl, and oxo; wherein the second aryl group, the heterocyclyl, and the heterocyclyl part of the heterocyclylalkyl can be further optionally substituted with one, two, three, four, or five substituents independently selected from alkoxy, alkyl, cyano, halo, haloalkoxy, haloalkyl, hydroxy, and nitro.

The term "arylalkyl," as used herein, refers to an alkyl group substituted with one, two, or three aryl groups.

The term "arylcarbonyl," as used herein, refers to an aryl group attached to the parent molecular moiety through a carbonyl group.

The term "aryloxy," as used herein, refers to an aryl group attached to the parent molecular moiety through an oxygen atom.

The term "aryloxycarbonyl," as used herein, refers to an aryloxy group attached to the parent molecular moiety through a carbonyl group.

The term "carbonyl," as used herein, refers to —C(O)—.

The term "carboxy," as used herein, refers to —CO$_2$H.

The term "carboxyalkyl," as used herein, refers to an alkyl group substituted with one, two, or three carboxy groups.

The term "cyano," as used herein, refers to —CN.

The term "cyanoalkyl," as used herein, refers to an alkyl group substituted with one, two, or three cyano groups.

The term "cycloalkenyl," as used herein, refers to an unsaturated, non-aromatic monocyclic hydrocarbon ring system having five to eight carbon atoms and zero heteroatoms.

The term "cycloalkyl," as used herein, refers to a saturated monocyclic, bicyclic, or tricyclic hydrocarbon ring system having three to fourteen carbon atoms and zero heteroatoms. Representative examples of cycloalkyl groups include, but are not limited to, cyclopropyl, cyclopentyl, bicyclo[3.1.1]heptyl, and adamantyl.

The term "(cycloalkyl)alkyl," as used herein, refers to an alkyl group substituted with one, two, or three cycloalkyl groups.

The term "cycloalkyloxy," as used herein, refers to a cycloalkyl group attached to the parent molecular moiety through an oxygen atom.

The term "cycloalkyloxycarbonyl," as used herein, refers to a cycloalkyloxy group attached to the parent molecular moiety through a carbonyl group.

The term "dialkylamino," as used herein, refers to —NR$^u$R$^v$, wherein R$^u$ and R$^v$ are the same or different alkyl groups.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkoxyalkyl," as used herein, refers to an alkyl group substituted with one, two, or three haloalkoxy groups.

The term "haloalkoxycarbonyl," as used herein, refers to a haloalkoxy group attached to the parent molecular moiety through a carbonyl group.

The term "haloalkyl," as used herein, refers to an alkyl group substituted with one, two, three, or four halogen atoms.

The term "heterocyclyl," as used herein, refers to a five-, six-, or seven-membered ring containing one, two, or three heteroatoms independently selected from nitrogen, oxygen, and sulfur. The five-membered ring has zero to two double bonds and the six- and seven-membered rings have zero to three double bonds. The term "heterocyclyl" also includes bicyclic groups in which the heterocyclyl ring is fused to a four- to six-membered aromatic or non-aromatic carbocyclic ring or another monocyclic heterocyclyl group. The heterocyclyl groups of the present disclosure are attached to the parent molecular moiety through a carbon atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, and thiomorpholinyl. The heterocyclyl groups of the present disclosure can be optionally substituted with one, two, three, four, or five substituents independently selected from alkoxy, alkoxycarbonyl, alkyl, aryl, cyano, halo, haloalkoxy, haloalkyl, a second heterocyclyl group, heterocyclylalkyl, hydroxy, hydroxyalkyl, nitro, —NR$^x$R$^y$, (NR$^x$R$^y$)alkoxy, (NR$^x$R$^y$)alkyl, (NR$^x$R$^y$)carbonyl, and oxo; wherein the aryl, the second heterocyclyl group, and the heterocyclyl part of the heterocyclylalkyl can be further optionally substituted with one, two, three, four, or five substituents independently selected from alkoxy, alkyl, cyano, halo, haloalkoxy, haloalkyl, hydroxy, and nitro.

The term "heterocyclylalkyl," as used herein, refers to an alkyl group substituted with one, two, or three heterocyclyl groups.

The term "heterocyclyloxy," as used herein, refers to a heterocyclyl group attached to the parent molecular moiety through an oxygen atom.

The term "heterocyclyloxycarbonyl," as used herein, refers to a heterocyclyloxy group attached to the parent molecular moiety through a carbonyl group.

The term "hydroxy," as used herein, refers to —OH.

The term "hydroxyalkyl," as used herein, refers to an alkyl group substituted with one, two, or three hydroxy groups.

The term "—NR$^a$R$^b$," as used herein, refers to two groups, R$^a$ and R$^b$, which are attached to the parent molecular moiety through a nitrogen atom. R$^a$ and R$^1$ are independently selected from hydrogen, alkenyl, alkoxyalkyl, alkyl, aryl, arylalkyl, cycloalkyl, (cycloalkyl)alkyl, heterocyclyl, and heterocyclylalkyl.

The term "(NR$^a$R$^b$)alkyl," as used herein, refers to an alkyl group substituted with one, two, or three —NR$^a$R$^b$ groups.

The term (NR$^a$R$^b$)carbonyl," as used herein, refers to an —NR$^a$R$^b$ group attached to the parent molecular moiety through a carbonyl group.

The term (NR$^a$R$^b$)sulfonyl," as used herein, refers to an —NR$^a$R$^b$ group attached to the parent molecular moiety through a sulfonyl group.

The term "—NR$^c$R$^d$," as used herein, refers to two groups, R$^c$ and R$^d$, which, taken together with the nitrogen atom to which they are attached, form a five- or six-membered monocyclic heterocyclic ring which is attached to the parent molecular moiety through the nitrogen atom.

The term "(NR$^c$R$^d$)alkyl," as used herein, refers to an alkyl group substituted with one, two, or three —NR$^c$R$^d$ groups.

The term (NR$^c$R$^d$)carbonyl," as used herein, refers to an —NR$^c$R$^d$ group attached to the parent molecular moiety through a carbonyl group.

The term (NR$^c$R$^d$)sulfonyl," as used herein, refers to an —NR$^c$R$^d$ group attached to the parent molecular moiety through a sulfonyl group.

The term "—NR$^x$R$^y$," as used herein, refers to two groups, R$^x$ and R$^y$, which are attached to the parent molecular moiety through a nitrogen atom. R$^x$ and R$^y$ are independently selected from hydrogen and alkyl.

The term "(NR$^x$R$^y$)alkoxy," as used herein, refers to an (NR$^x$R$^y$)alkyl group attached to the parent molecular moiety through an oxygen atom.

The term "(NR$^x$R$^y$)alkyl," as used herein, refers to an alkyl group substituted with one, two, or three —NR$^x$R$^y$ groups.

The term (NR$^x$R$^y$)carbonyl," as used herein, refers to an —NR$^x$R$^y$ group attached to the parent molecular moiety through a carbonyl group.

The term "nitro," as used herein, refers to —NO$_2$.

The term "oxo," as used herein, refers to =O.

The term "sulfonyl," as used herein, refers to —SO$_2$—.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

As used herein, the term "anti-HCV activity" means the compound is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

The term "compounds of the disclosure", and equivalent expressions, are meant to embrace compounds of formula (I), and pharmaceutically acceptable enantiomers, diastereomers, and salts thereof. Similarly, references to intermediates, are meant to embrace their salts where the context so permits.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The term "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

The term "residue" with reference to an amino acid or amino acid derivative means a radical derived from the corresponding α-amino acid by eliminating the hydroxy of the carboxy group and one hydrogen of the α-amino acid group. For instance, the terms Gln, Ala, Gly, Ile, Arg, Asp, Phe, Ser, Leu, Cys, Asn, Sar and Tyr represent the "residues" of L-glutamine, L-alanine, glycine, L-isoleucine, L-arginine, L-aspartic acid, L-phenylalanine, L-serine, L-leucine, L-cysteine, L-asparagine, sarcosine and L-tyrosine, respectively.

The term "side chain" with reference to an amino acid or amino acid residue means a group attached to the α-carbon atom of the α-amino acid. For example, the R-group side chain for glycine is hydrogen, for alanine it is methyl, for valine it is isopropyl. For the specific R-groups or side chains of the α-amino acids reference is made to A. L. Lehninger's text on Biochemistry (see chapter 4).

Where used in naming compounds of the present disclosure, the designations P1', P1, P2, P2*, P3, and P4, as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend toward the C-terminus. For example, P1' refers to the first position away from the right hand end of the C-terminus of the cleavage site (i.e. N-terminus first position); whereas P1 starts the numbering from the left hand side of the C-terminus cleavage site, P2: second position from the C-terminus, etc.). (see Berger A. & Schechter I., Transactions of the Royal Society London series (1970), B257, 249-264].

The following FIGURE shows the designations for the compounds of the present disclosure.

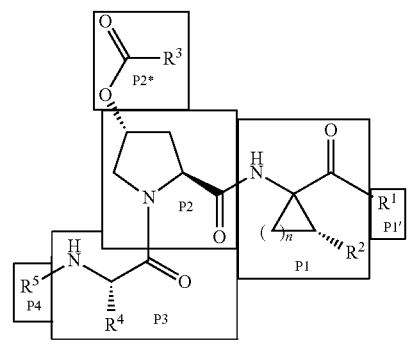

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

Certain illustrative HCV inhibitor compounds which can be administered with the compounds of the present disclosure include those disclosed in the following publications: WO 02/04425 A2 published Jan. 17, 2002, WO 03/007945 A1 published Jan. 30, 2003, WO 03/010141 A2 published Feb. 6, 2003, WO 03/010142 A2 published Feb. 6, 2003, WO 03/010143 A1 published Feb. 6, 2003, WO 03/000254 A1 published Jan. 3, 2003, WO 01/32153 A2 published May 10, 2001, WO 00/06529 published Feb. 10, 2000, WO 00/18231 published Apr. 6, 2000, WO 00/10573 published Mar. 2, 2000, WO 00/13708 published Mar. 16, 2000, WO 01/85172 A1 published Nov. 15, 2001, WO 03/037893 A1 published May 8, 2003, WO 03/037894 A1 published May 8, 2003, WO 03/037895 A1 published May 8, 2003, WO 02/100851 A2 published Dec. 19, 2002, WO 02/100846 A1 published Dec. 19, 2002, EP 1256628 A2 published Nov. 13, 2002, WO 99/01582 published Jan. 14, 1999, WO 00/09543 published Feb. 24, 2000.

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
| --- | --- | --- | --- |
| NIM811 | | Cyclophilin Inhibitor | Novartis |
| Zadaxin | | Immunomodulator | Sciclone |
| Suvus | | Methylene blue | Bioenvision |
| Actilon (CPG10101) | | TLR9 agonist | Coley |

TABLE 1-continued

| Brand Name | Physiological Class | Type of Inhibitor or Target | Source Company |
|---|---|---|---|
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |

TABLE 1-continued

| Brand Name | Physiological Class | Type of Inhibitor or Target | Source Company |
|---|---|---|---|
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immunosuppressant | F. Hoffmann-La Roche LTD, Basel, Switzerland |
| Civacir | Immunosuppressant | HCV IgG immunosuppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharmiceuticals Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |

TABLE 1-continued

| Brand Name | Physiological Class | Type of Inhibitor or Target | Source Company |
|---|---|---|---|
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen|Valentis |
| Wellferon | Interferon | lymphoblastoid IFN-αn1 | GlaxoSmith Kline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |

The compounds of the disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: Boc for tert-butoxycarbonyl; Boc$_2$O or (Boc)$_2$O for di-tert-butyl dicarbonate; CDI for 1,1'-carbonyldiimidazole; DBU for 1,8-diazabicyclo[5.4.0]undec-7-ene; DMAP or 4-DMAP for 4-N,N-dimethylaminopyridine; DMSO for dimethylsulfoxide; DPPA for diphenylphosphoryl azide; EDAC or EDC for 1-(3-dimethylaminopropyl)-3-ethylcarbodiimide hydrochloride; Et for ethyl; Et$_3$N for triethylamine; Fmoc for 9-fluorenylmethoxycarbonyl; HATU for O-(7-azabenzotriazol-1-yl)-N,N,N',N'-tetramethyluronium phosphate; HOBt for 1-hydroxybenzotriazole; LiHMDS for lithium hexamethyldisilazide; Me for methyl; MeI for methyl iodide; MeO for methoxy; OAc for acetate; OtBu for tert-butoxy; rt for room temperature; PyBOP for benzotriazol-1-yl-oxy-tris-pyrrolidino-phosphoniumhexafluorophosphate; TBAF for tetrabutylammonium fluoride; TBME or MTBE for tert-butyl methyl ether; TFA for trifluoroacetic acid; and THF for tetrahydrofuran.

The compounds of the present disclosure may contain two or more chiral centers. For example, the compounds may include a P1 cyclopropyl element

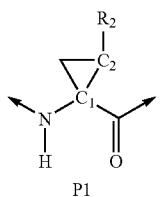

P1 wherein $C_1$ and $C_2$ each represent an asymmetric carbon atom at positions 1 and 2 of the cyclopropyl ring. Notwithstanding other possible asymmetric centers at other segments of the compounds, the presence of these two asymmetric centers means that the compounds can exist as racemic mixtures of diastereomers, such as the diastereomers wherein $R_2$ is configured either syn to the amide or syn to the carbonyl. These said diastereosiomers and their enantiomeric forms are designated below.

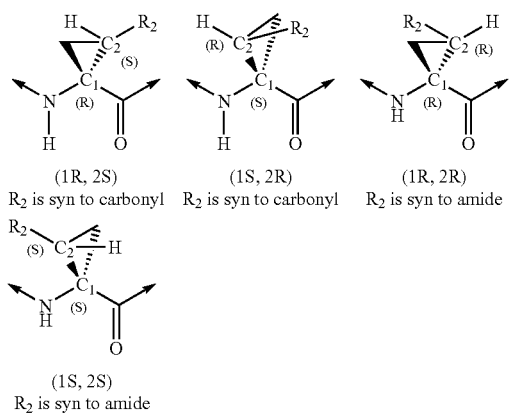

It should be understood that the present disclosure encompasses all stereochemical isomeric forms, or mixtures thereof, which possess the ability to inhibit HCV protease. Enantiomers of the present disclosure may be resolved by methods known to those skilled in the art, for example, by formation of diastereoisomeric salts which may be separated by crystallization, gas-liquid or liquid chromatography, or selective reaction of one enantiomer with an enantiomer-specific reagent. It will be appreciated that where the desired enantiomer is converted into another chemical entity by a separation technique, then an additional step is required to form the desired enantiomeric form. Alternatively, specific enantiomers may be synthesized by asymmetric synthesis using optically active reagents, substrates, catalysts or solvents, or by converting one enantiomer into the other by asymmetric transformation.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure may exist in zwitterionic form and the present disclosure includes each zwitterionic form of these compounds and mixtures thereof.

The starting materials useful to synthesize the compounds of the present disclosure are known to those skilled in the art and can be readily manufactured or are commercially available.

The following methods set forth below are provided for illustrative purposes and are not intended to limit the scope of the claimed disclosure. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

The compounds of the present disclosure may, for example, be synthesized according to a general process as illustrated in Scheme I (wherein CPG is a carboxyl protecting group and APG is an amino protecting group).

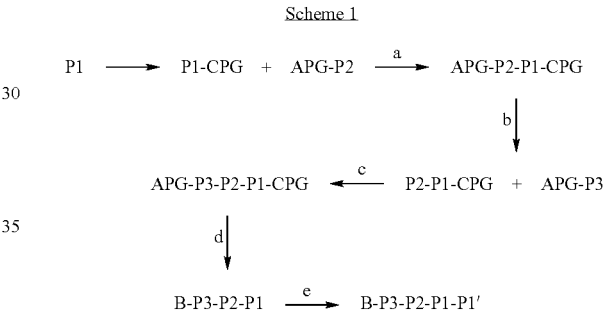

Briefly, the P1', P1, P2, P3 and P4 can be linked by well known peptide coupling techniques. The P1', P1, P2, P3 and P4 groups may be linked together in any order as long as the final compound corresponds to peptides of the disclosure. For example, P3 can be linked to P2-P1; or P1 linked to P3-P2.

Generally, peptides are elongated by deprotecting the α-amino group of the N-terminal residue and coupling the unprotected carboxyl group of the next suitably N-protected amino acid through a peptide linkage using the methods described. This deprotection and coupling procedure is repeated until the desired sequence is obtained. This coupling can be performed with the constituent amino acids in step-wise fashion, as depicted in Scheme I.

Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxysuccinimido ester) method, Woodward reagent K-method, carbonyldiimidazole method, phosphorus reagents or oxidation-reduction methods. Some of these methods (especially the carbodiimide method) can be enhanced by adding 1-hydroxybenzotriazole or 4-DMAP. These coupling reactions can be performed in either solution (liquid phase) or solid phase.

More explicitly, the coupling step involves the dehydrative coupling of a free carboxyl of one reactant with the free amino group of the other reactant in the present of a coupling agent to form a linking amide bond. Descriptions of such coupling agents are found in general textbooks on peptide chemistry, for example, M. Bodanszky, "Peptide Chemistry", $2^{nd}$ rev ed., Springer-Verlag, Berlin, Germany, (1993). Examples of suitable coupling agents are N,N'-dicyclohexylcarbodiimide, 1-hydroxybenzotriazole in the presence of N,N'-dicyclohexylcarbodiimide or N-ethyl-N'-[(3-dimethylamino)propyl]carbodiimide. A practical and useful coupling agent is the commercially available (benzotriazol-1-yloxy)tris-(dimethylamino)phosphonium hexafluorophosphate, either by itself or in the present of 1-hydroxybenzotriazole or 4-DMAP. Another practical and useful coupling agent is commercially available 2-(1H-benzotriazol-1-yl)-N,N,N',N'-tetramethyluronium tetrafluoroborate. Still another practical and useful coupling agent is commercially available O-(7-azabenzotriazol-1-yl)-N,N,N',N'-tetramethyluronium hexafluorophosphate.

The coupling reaction is conducted in an inert solvent, e.g. dichloromethane, acetonitrile or dimethylformamide. An excess of a tertiary amine, e.g. diisopropylethylamine, N-methylmorpholine, N-methylpyrrolidine or 4-DMAP is added to maintain the reaction mixture at a pH of about 8. The reaction temperature usually ranges between 0° C. and 50° C. and the reaction time usually ranges between 15 minutes and 24 hours.

The functional groups of the constituent amino acids generally must be protected during the coupling reactions to avoid formation of undesired bonds. Protecting groups that can be used are listed, for example, in Greene, "Protective Groups in Organic Chemistry", third edition, John Wiley & Sons, New York and "The Peptides: Analysis, Synthesis, Biology", Vol. 3, Academic Press, New York (1981).

The α-amino group of each amino acid to be coupled to the growing peptide chain must be protected (APG). Any protecting group known in the art can be used. Examples of such groups include: 1) acyl groups such as formyl, trifluoroacetyl, phthalyl, and p-toluenesulfonyl; 2) aromatic carbamate groups such as benzyloxycarbonyl (Cbz or Z) and substituted benzyloxycarbonyls, and 9-fluorenylmethyloxycarbonyl (Fmoc); 3) aliphatic carbamate groups such as tert-butyloxycarbonyl (Boc), ethoxycarbonyl, diisopropylmethoxycarbonyl, and allyloxycarbonyl; 4) cyclic alkyl carbamate groups such as cyclopentyloxycarbonyl and adamantyloxycarbonyl; 5) alkyl groups such as triphenylmethyl and benzyl; 6) trialkylsilyl such as trimethylsilyl; and 7) thiol containing groups such as phenylthiocarbonyl and dithiasuccinoyl.

In one embodiment the α-amino protecting group is either Boc or Fmoc. Many amino acid derivatives suitably protected for peptide synthesis are commercially available.

The α-amino protecting group of the newly added amino acid residue is cleaved prior to the coupling of the next amino acid. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature (rt or RT) usually 20-22° C.

Any of the amino acids having side chain functionalities must be protected during the preparation of the peptide using any of the above-described groups. Those skilled in the art will appreciate that the selection and use of appropriate protecting groups for these side chain functionalities depend upon the amino acid and presence of other protecting groups in the peptide. The selection of such protecting groups is important in that the group must not be removed during the deprotection and coupling of the α-amino group.

For example, when Boc is used as the α-amino protecting group, the following side chain protecting group are suitable: p-toluenesulfonyl (tosyl) moieties can be used to protect the amino side chain of amino acids such as Lys and Arg; acetamidomethyl, benzyl (Bn), or tert-butylsulfonyl moieties can be used to protect the sulfide containing side chain of cysteine; benzyl (Bn) ethers can be used to protect the hydroxy containing side chains of serine, threonine or hydroxyproline; and benzyl esters can be used to protect the carboxy containing side chains of aspartic acid and glutamic acid.

When Fmoc is chosen for the α-amine protection, usually tert-butyl based protecting groups are acceptable. For instance, Boc can be used for lysine and arginine, tert-butyl ether for serine, threonine and hydroxyproline, and tert-butyl ester for aspartic acid and glutamic acid. Triphenylmethyl (Trityl) moiety can be used to protect the sulfide containing side chain of cysteine.

Once the elongation of the peptide is completed all of the protecting groups are removed. These procedures are well known to those skilled in the art.

Further, the following guidance may be followed in the preparation of compounds of the present disclosure. For example, to form a compound where $R^6$ is alkylcarbonyl or alkylsulfonyl, a protected P3 or the whole peptide or a peptide segment is coupled to an appropriate acyl chloride or sulfonyl chloride respectively, that is either commercially available or for which the synthesis is well known in the art.

In preparing a compound where $R^5$ is alkoxycarbonyl, a protected P3 or the whole peptide or a peptide segment is coupled to an appropriate chloroformate that is either commercially available or for which the synthesis is well known in the art. For Boc-derivatives $(Boc)_2O$ is used.

For example:

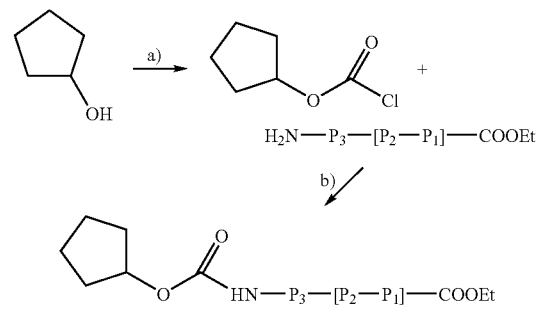

In this example, cyclopentanol is treated with phosgene to furnish the corresponding chloroformate which is treated with either a protected P3 or the whole peptide or a peptide segment to provide the corresponding carbamate.

The chloroformate is treated with the desired $NH_2$-tripeptide in the presence of a base such as triethylamine to afford the cyclopentylcarbamate.

In preparing a compound where $R^5$ is $(NR^aR^b)$carbonyl a protected P3 or the whole peptide or a peptide segment is treated with phosgene followed by amine as described in *Syn*.

*Lett.* February 1995; (2); 142-144 or is reacted with the commercially available isocyanate and a suitable base such as triethylamine.

In preparing a compound where $R^5$ is $(NR^aR^b)$sulfonyl, a protected P3 or the whole peptide or a peptide segment is treated with either a freshly prepared or commercially available sulfamyl chloride followed by amine as described in WO 98/32748.

The α-carboxyl group of the C-terminal residue is usually protected as an ester (CPG) that can be cleaved to give the carboxylic acid. Protecting groups that can be used include: 1) alkyl esters such as methyl, trimethylsilylethyl and tert-butyl, 2) alkylaryl esters such as benzyl and substituted benzyl, or 3) esters that can be cleaved by mild base treatment or mild reductive means such as trichloroethyl and phenacyl esters.

The resulting α-carboxylic acid (resulting from cleavage by mild acid, mild base treatment or mild reductive means) is coupled with a $R^6SO_2NH_2$ (prepared by treatment of $R^6SO_2Cl$ in ammonia saturated tetrahydrofuran solution) in the presence of peptide coupling agent such as CDI or EDAC in the presence of a base such as 4-dimethylaminopyridine (4-DMAP) and/or 1,8-diazabicyclo[5.4.0]undec-7-ene (DBU) to incorporate the P1' moiety, effectively assembling the tripeptide P1'-P1-P2-P3-APG. Typically, in this process, 1-5 equivalents of P1' coupling agents are used.

Furthermore, if the P3 protecting group APG is removed and replaced with a P4 moiety by the methods described above, and the resulting α-carboxylic acid resulting from cleavage (resulting from cleavage by mild acid, mild base treatment or mild reductive means) is coupled with a $R^6SO_2NH_2$ (prepared by treatment of $R^6SO_2Cl$ in ammonia saturated tetrahydrofuran solution or alternative methods described herein) in the presence of peptide coupling agent such as CDI or EDAC in the presence of a base such as 4-dimethylaminopyridine (4-DMAP) and/or 1,8-diazabicyclo[5.4.0]undec-7-ene (DBU) to incorporate the P1' moiety, the tripeptide P1'-P1-P2-P3-P4 is prepared. Typically, in this process, 1-5 equivalents of P1' coupling agents are used.

Scheme II further shows the general process wherein compounds of formula (I) are constructed by the coupling of tripeptide carboxylic acid with a P1' sulfonamide. Said coupling reaction requires treatment of carboxylic acid (1) with a coupling reagent such as carbonyl diimidazole in a solvent such as THF, which can be heated to reflux, followed by the addition of the formed derivative of (1), to the P1' sulfonamide, in a solvent such as THF or dichloromethane in the presence of a base such as DBU.

Scheme II

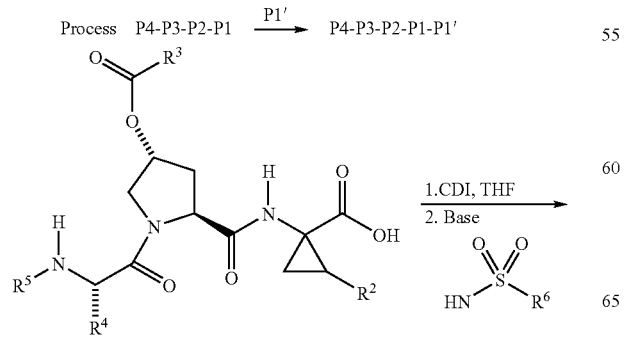

An alternative process for the construction of compounds of formula (I) is shown in Scheme III. The P1' sulfonamide element is coupled to the P1 element using the process employed in Scheme I. The resulting P1-P1' moiety can then be deprotected at its amino terminus. In this general example a Boc protecting group is employed but one skilled in the art would recognize that a number of suitable amino protecting groups could be employed in this process. The Boc protecting group can be removed using acid such as trifluoroacetic acid in a solvent such as dichloroethane to provide the deprotected amine as the TFA salt. The TFA amine salt can be directly employed in the subsequent coupling reaction or as an alternative the TFA amine salt can be first converted to the HCl amine salt, which can be used in said coupling reaction as shown in Scheme III. The coupling of the HCl amine salt (3) with the carboxyl terminus a P4-P3-P2 intermediate can be achieved using coupling reagents, such as HATU, in solvents such as dichloromethane to provide compounds of formula (I) (4).

Scheme III

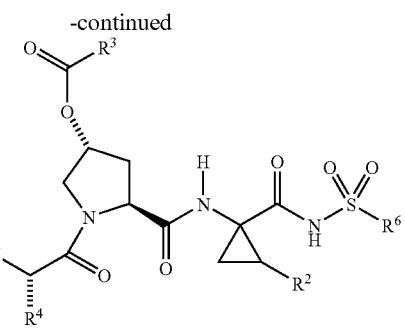

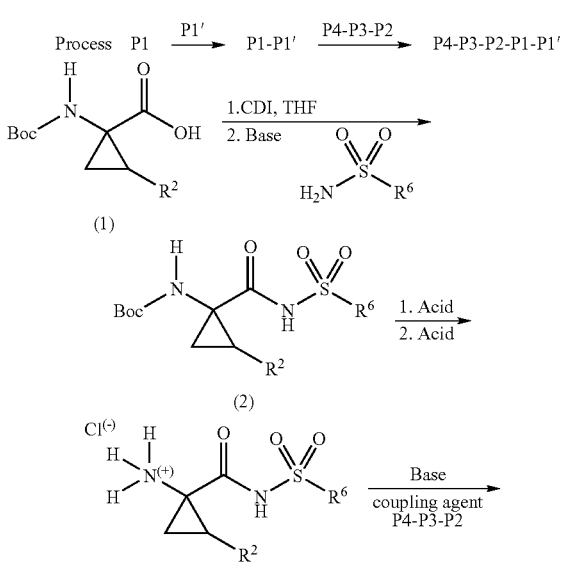

Compounds of formula (I)

An alternative process for the construction of compounds of formula (I) is shown in Scheme IV. Herein the hydrochloride salt of the P1-P1' terminal amine (1) is coupled to the free carboxyl group of the P2 element using coupling agents such as PyBOP, in the presence of a base such as diisopropyl amine, and in a solvent such as dichloromethane. The resulting P2-P1-P1' intermediate can be converted to compounds of formula (I) in a two step process wherein the first step is deprotection of the P2 amine terminus using an acid such as TFA in a solvent such as dichloromethane. The resulting trifluoroacetic acid salt can be coupled with the carboxyl terminus of the P4-P3 element using standard coupling agents such as PyBOP in the presence of base such as diisopropyl amine, and using solvents such as dichloromethane to provide compounds of formula (I) (4).

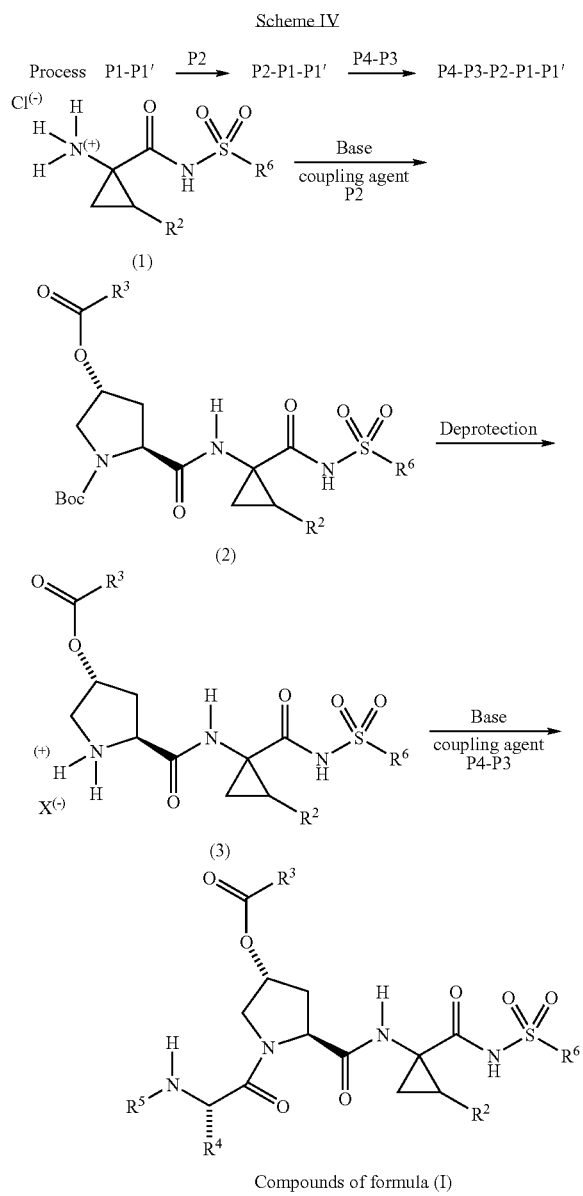

One skilled in the art would recognize that the incorporation of P2* into the molecule can be carried out at any stage in the assembly of the peptide backbone. This is illustrated in Scheme V for the conversion of intermediates such as 1 and 3 into compounds of formula (I). In such reactions acid chlorides can be used as acylating agents in the presence of an amine such as triethylamine and in a solvent such as dichloromethane. In some examples it may be necessary to heat the reaction or alternatively to add a catalyst such as DMAP.

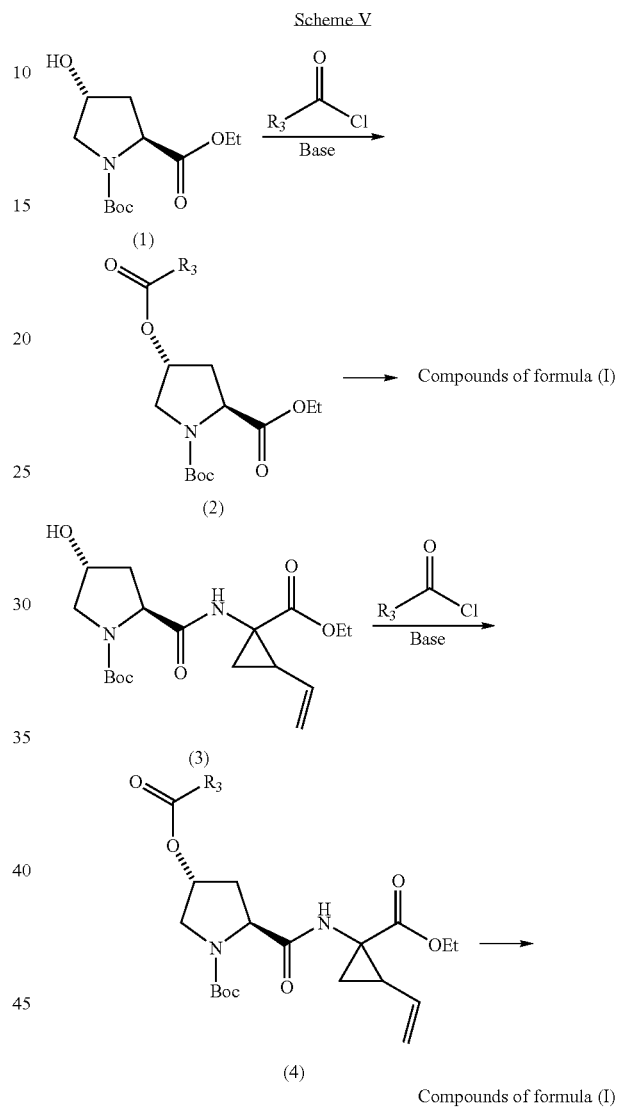

Compounds of formula (I) can also be converted into other compounds of formula (I) as described herein. An example of such a process is shown in Scheme VI where a compound of formula (I) (1) which bears a Boc group at the P4 position is converted to a compound of formula (I) (3) wherein said compound bears a urea group at the P4 position. The conversion of (1) to (3) can be carried out in a two step process the first of which is the conversion of (1) to amine (2) by treatment of (1) with an acid such as TFA in a solvent such as dichloromethane. The resulting amine TFA salt can be treated with an isocyanate such as tert-butylisocyanate in the presence of one equivalent of base to provide a compound of formula (I) (3) wherein the P3 moiety is capped with a urea. As previously noted one skilled in the art will recognize that intermediate (2) can be used as starting materials for the preparation of compounds of formula (I) wherein the P3 group is capped with an amide or a sulfonamide, or thiourea, or a sulfamide. The construction of said compounds of formula (I) can be achieved using standard conditions for the formation of said P4 functionalities from amines.

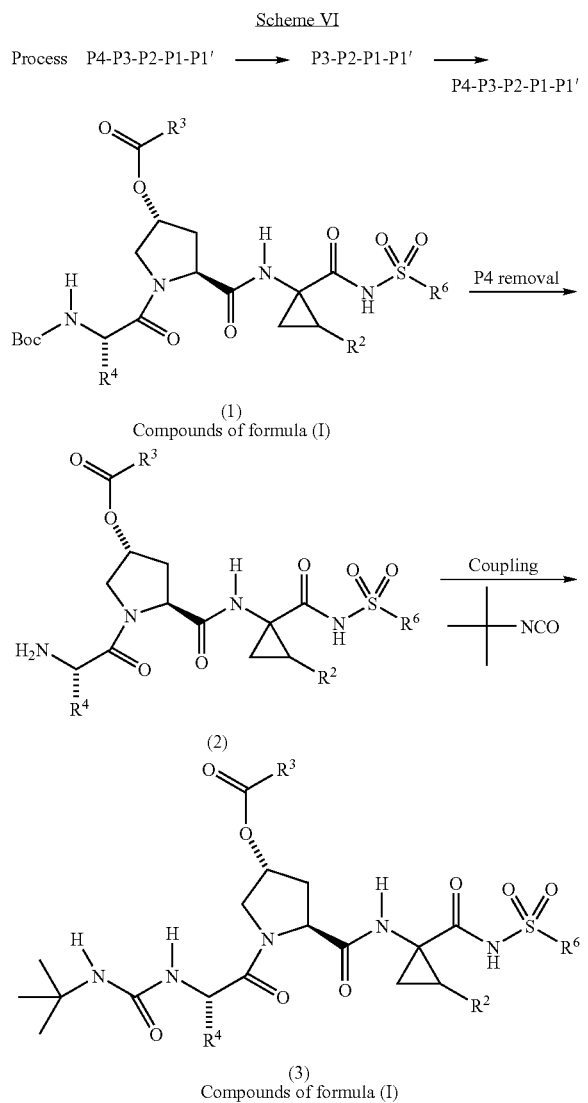

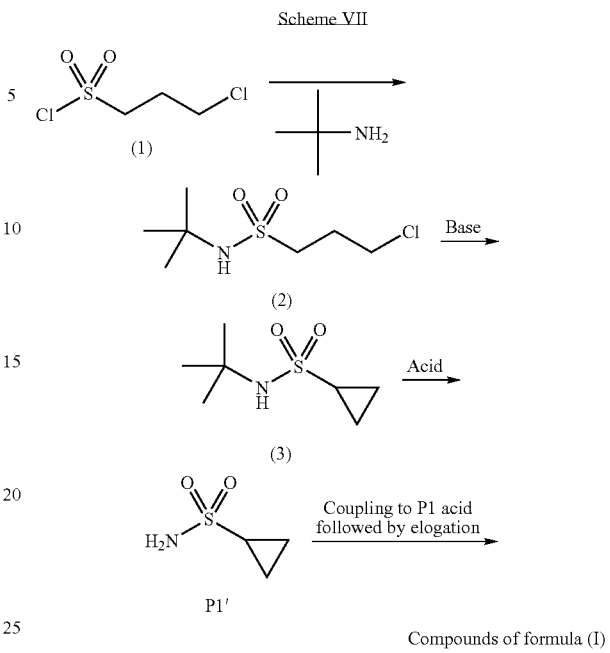

Substituted cycloalkylsulfonamides can also be incorporated into compounds of formula (I) using a modification of the above said procedure. For example, intermediate 2 of Scheme VIII can be treated with two equivalents of base such as butyllithium and the resulting reaction mixture can be treated with an electrophile such as methyl iodide to provide a substituted cycloalkylsulfonamide (3). This intermediate (3) can be deprotected at the N-terminus and the resulting compound (4) utilized as an intermediate in the preparation of compounds of formula (I).

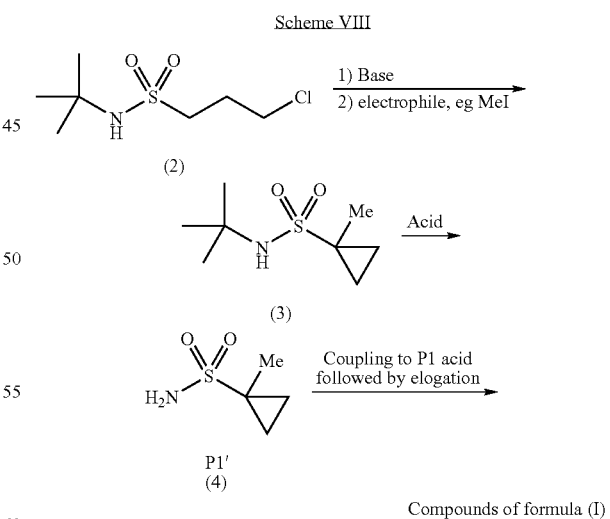

Compounds of formula (I)

In the construction of compounds of formula (I), the P1' terminus is incorporated into the molecules using one of the general processes outlined above and described in more detail below. In some examples the P1' elements are cycloalkyl- or alkylsulfonamides which are commercially available or can be prepared from the corresponding alkyl- or cycloalkylsulfonyl chloride by treating said sulfonyl chloride with ammonia. Alternatively, these sulfonamides can be synthesized using the general process outline in Scheme VII. Therein commercially available 3-chloropropylsulfonyl chloride (1) is converted to a suitable protected sulfonamide as for example by treatment with tert-butyl amine. The sulfonamide obtained (2) is then converted to the corresponding cycloalkylsulfonamide by treatment with two equivalents of a base such as butyllithium in a solvent such as THF. The resulting cycloalkylsulfonamide can be deprotected by treatment with an acid to provide the desired unprotected cycloalkylsulfoamide.

The P1' intermediates employed in generating compounds of formula (I) are in some cases derived from sulfamide derivatives. In such cases the sulfamide intermediates are available by several synthetic routes as for example by the pathway outlined in Scheme IX.

Scheme IX

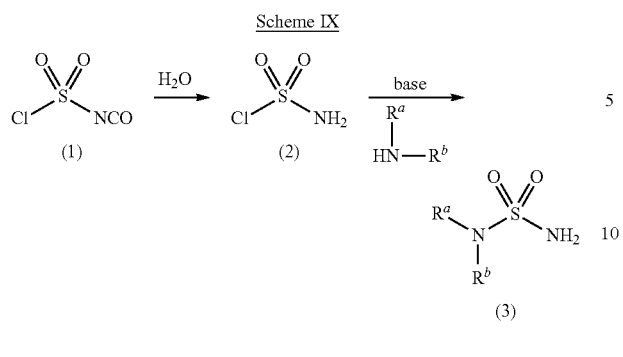

Sulfamoyl chloride (2) can be prepared in situ by the addition of water (e.g. 1 equiv) to chlorosulfonyl isocyanate 1 (e.g. 1 equiv) in a solvent such as THF, maintained at a low temperature such as −20° C., and the resulting solution is allowed to warm to 0° C. To this solution a base, such as anhydrous triethylamine (eg., 1 equiv), is added followed by an amine (eg., 1 equiv). The reaction mixture is then warmed to room temperature, filtered and the filtrate concentrated to afford the desired sulfamides (3).

The sulfamides can be incorporated into compounds of formula (I) following the synthetic pathway defined in Scheme X. Therein, a carboxylic acid P1 element (1) is treated with an activating agent such as CDI. In a separate flask, a strong base is added to a solution of the above described sulfamide and the resulting reaction mixture is stirred for several hours after which this reaction mixture is added to the flask containing the activated carboxylic acid, to provide acylsulfamide derivatives (2). Intermediates like 2 can be converted to compounds of formula (I) as described herein.

Scheme X

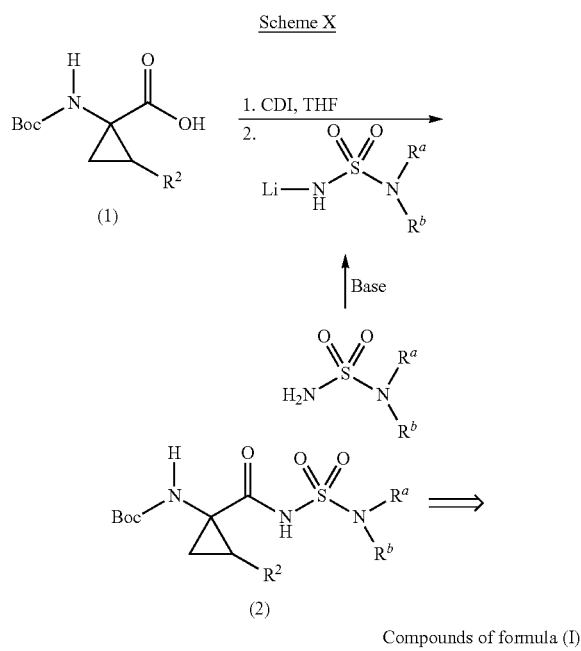

It should be noted that acylsulfamide derivatives can also be prepared from tripeptide carboxylic acids in a one step process as defined in Scheme XI.

Scheme XI

Process P4-P3-P2-P1 $\xrightarrow{P1'}$ P4-P3-P2-P1-P1'

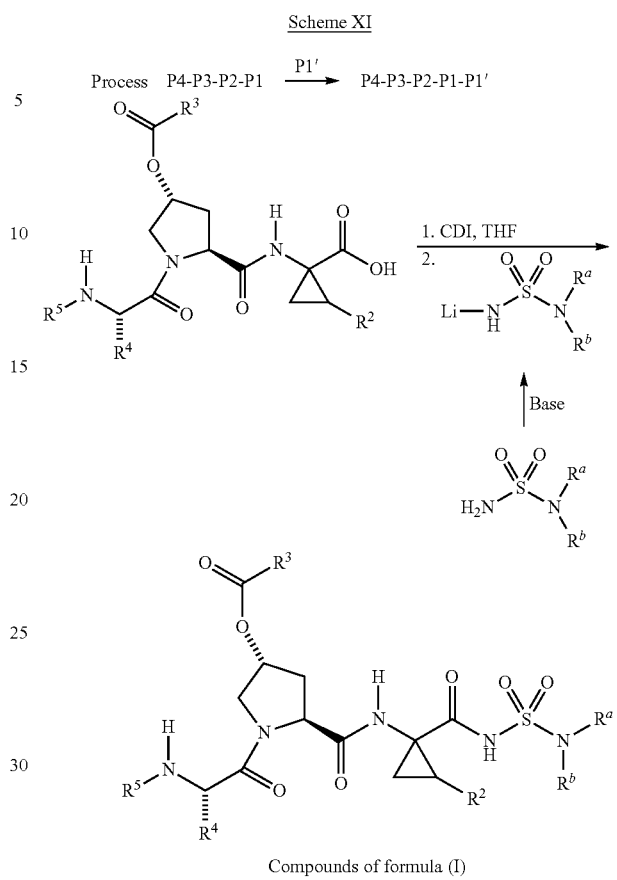

Compounds of formula (I)

The P1 elements utilized in generating compounds of formula (I) are in some cases commercially available, but are otherwise synthesized using the methods known to one skilled in the art and in a non-limiting sense described herein and subsequently incorporated into compounds of formula (I) using the methods described herein. The substituted P1 cyclopropylamino acids can be synthesized following the general process outline in Scheme XII.

Treatment of commercially available or easily synthesized imine (1) with 1,4-dihalobutene (2) in presence of a base produces, provides the resulting imine (3). Acid hydrolysis of (3) then provides (4), which has an allyl substituent syn to the carboxyl group as a major product. The amine moiety of (4) can protected using a Boc group to provide the fully protected amino acid (5). This intermediate is a racemate which can be resolved by an enzymatic process wherein the ester moiety of (5) is cleaved by a protease to provide the corresponding carboxylic acid. Without being bound to any particular theory, it is believed that this reaction is selective in that one of the enantiomers undergoes the reaction at a much greater rate than its mirror image providing for a kinetic resolution of the intermediate racemate. In an embodiment of the examples cited herein, the stereoisomer for integration into compounds of formula (I) is (5a) which houses the (1R, 2S) stereochemistry. In the presence of the enzyme, this enantiomer does not undergo ester cleavage and thereby this enantiomer (5a) is recovered from the reaction mixture. However, the other enantiomer, (5b) which houses the (1S, 2R) stereochemistry undergoes ester cleavage, i.e., hydrolysis, to provide the free acid (6). Upon completion of this reaction, ester (5a) can be separated from the acid product (6) by routine methods such as, for example, aqueous extraction methods or chromatography.

Scheme XII

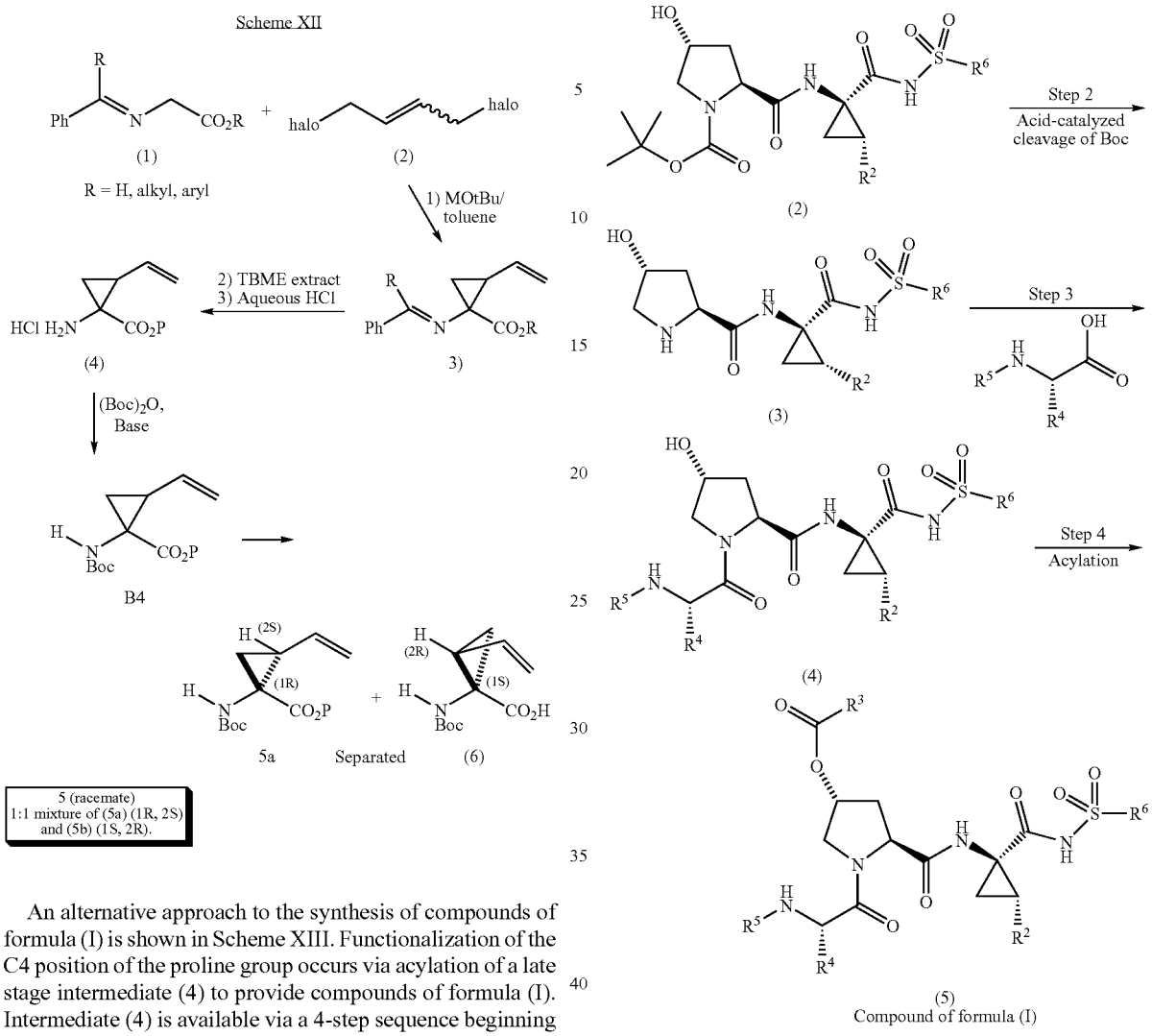

An alternative approach to the synthesis of compounds of formula (I) is shown in Scheme XIII. Functionalization of the C4 position of the proline group occurs via acylation of a late stage intermediate (4) to provide compounds of formula (I). Intermediate (4) is available via a 4-step sequence beginning with commercially available intermediate (1), the first step of which involves coupling of (1) to a P1-P1' intermediate coupling reagents established in the art. Acid-catalyzed deprotection of the N-Boc group of intermediate (2) provides free amine intermediate (3) which is subsequently coupled with the P3-P4 fragment to provide intermediate (4). The selective acylation of the C4 hydroxy group in intermediate (4) to provide compounds of formula 1 (5) can be achieved using acylating agents such as acid chlorides in the presence of a base such as diisopropylethyl amine. In some examples it may be necessary to add a catalyst such as DMAP.

Scheme XIII

EXAMPLES

The present disclosure will now be described in connection with certain preferred embodiments which are not intended to limit its scope. On the contrary, the present disclosure covers all alternatives, modifications, and equivalents as can be included within the scope of the claims. Thus, the following examples, which include specific embodiments, will illustrate one practice of the present invention, it being understood that the examples are for the purposes of illustration of certain embodiments and are presented to provide what is believed to be the most useful and readily understood description of its procedures and conceptual aspects.

Solution percentages express a weight to volume relationship, and solution ratios express a volume to volume relationship, unless stated otherwise. Nuclear magnetic resonance (NMR) spectra were recorded either on a Bruker 300, 400, or 500 MHz spectrometer; the chemical shifts (δ) are reported in parts per million. Flash chromatography was carried out on silica gel ($SiO_2$) according to Still's flash chromatography technique (*J. Org. Chem.* 1978, 43, 2923).

Section A: Preparation of Intermediates

I. Preparation of P1 Intermediates

1. Preparation of (1R,2S)/(1S,2R) 1-amino-2-vinyl-cyclopropane carboxylic acid ethyl ester (racemic mixture): Method 1 (of 2)

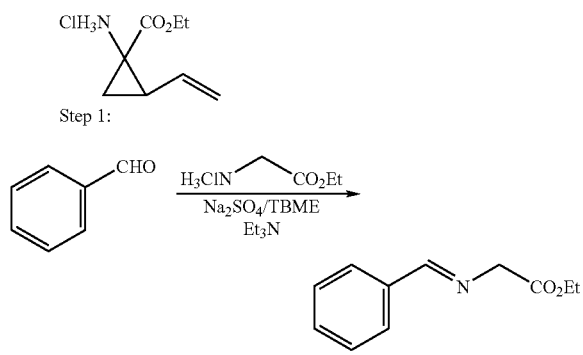

Step 1:

Glycine ethyl ester hydrochloride (303.8 g, 2.16 mol) was suspended in tert-butyl methyl ether (1.6 L). Benzaldehyde (231 g, 2.16 mol) and anhydrous sodium sulfate (154.6 g, 1.09 mol) were added and the mixture cooled to 0° C. using an ice-water bath. Triethylamine (455 mL, 3.26 mol) was added dropwise over 30 minutes and the mixture was stirred for 48 hours at room temperature. The reaction was then quenched by addition of ice-cold water (1 L) and the organic layer was separated. The aqueous phase was extracted with tert-butyl methyl ether (0.5 L) and the combined organic phases were washed with a mixture of saturated aqueous NaHCO₃ (1 L) and brine (1 L). The solution was dried over MgSO₄, filtered, and concentrated in vacuo to afford 392.4 g of the N-benzyl imine product as a thick yellow oil that was used directly in the next step. $^1$H NMR (CDCl₃, 300 MHz) δ 1.32 (t, J=7.1 Hz, 3H), 4.24 (q, J=7.1 Hz, 2H), 4.41 (d, J=1.1 Hz, 2H), 7.39-7.47 (m, 3H), 7.78-7.81 (m, 2H), 8.31 (s, 1H).

Step 2:

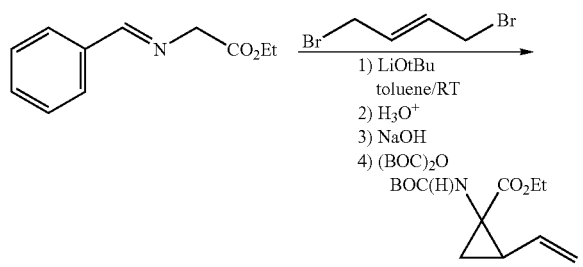

To a suspension of lithium tert-butoxide (84.06 g, 1.05 mol) in dry toluene (1.2 L), was added dropwise a mixture of the product of Step 1 (100.4 g, 0.526 mol) and trans-1,4-dibromo-2-butene (107.0 g, 0.500 mol) in dry toluene (0.6 L) over 60 minutes. After completion of the addition, the deep red mixture was quenched by addition of water (1 L) and tert-butyl methyl ether (TBME, 1 L). The aqueous phase was separated and extracted a second time with TBME (1 L). The organic phases were combined, 1N HCl (1 L) was added, and the mixture was stirred at room temperature for 2 hours. The organic phase was separated and extracted with water (0.8 L). The aqueous phases were then combined, saturated with salt (700 g), treated with TBME (1 L), and cooled to 0° C. The stirred mixture was then adjusted to pH 14 by the dropwise addition of 10N NaOH, the organic layer separated, and the aqueous phase extracted with TBME (2×500 mL). The combined organic extracts were dried (MgSO₄), filtered, and concentrated to a volume of 1 L. To this solution of free amine was added di-tert-butyldicarbonate (131.0 g, 0.6 mol) and the mixture was stirred 4 days at room temperature. Additional di-tert-butyldicarbonate (50 g, 0.23 mol) was added to the reaction, the mixture was heated to reflux for 3 hours, and was then allowed cool to room temperature overnight. The reaction mixture was dried over MgSO₄, filtered, and concentrated in vacuo to afford 80 g of crude material. This residue was purified by flash chromatography (2.5 kg of SiO₂, eluted with 1% to 2% methanol/dichloromethane) to afford 57 g (53%) of (1R,2S)/(1S,2R) N-Boc-1-amino-2-vinylcyclopropane carboxylic acid ethyl ester as a yellow oil which solidified while sitting in the refrigerator: $^1$H NMR (CDCl₃, 300 MHz) δ 1.26 (t, J=7.1 Hz, 3H), 1.46 (s, 9H), 1.43-1.49 (m, 1H), 1.76-1.82 (br m, 1H), 2.14 (q, J=8.6 Hz, 1H), 4.18 (q, J=7.2 Hz, 2H), 5.12 (dd J=10.3, 1.7 Hz, 1H), 5.25 (br s, 1H), 5.29 (dd, J=17.6, 1.7 Hz, 1H), 5.77 (ddd, J=17.6, 10.3, 8.9 Hz, 1H); MS m/z 254.16 (M−1).

Step 3:

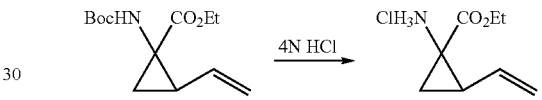

The product of Step 2 (9.39 g, 36.8 mmol) was dissolved in 4N HCl/dioxane (90 mL, 360 mmol) and was stirred for 2 hours at room temperature. The reaction mixture was concentrated to provide (1R,2S)/(1S,2R) 1-amino-2-vinylcyclopropane carboxylic acid ethyl ester hydrochloride in quanitative yield (7 g, 100%). $^1$H NMR (methanol-d₄) δ 1.32 (t, J=7.1, 3H), 1.72 (dd, J=10.2, 6.6 Hz, 1H), 1.81 (dd, J=8.3, 6.6 Hz, 1H), 2.38 (q, J=8.3 Hz, 1H), 4.26-4.34 (m, 2H), 5.24 (dd, 10.3, 1.3 Hz, 1H) 5.40 (d, J=17.2, 1H), 5.69-5.81 (m, 1H).

Alternate Route for the Preparation of Racemic N-Boc-1-amino-2-vinylcyclopropane Carboxylic Acid Ethyl Ester Hydrochloride: Method 2 (of 2)

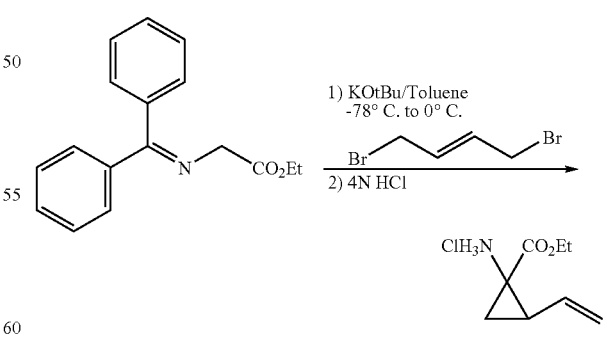

To a solution of potassium tert-butoxide (11.55 g, 102.9 mmol) in THF (450 mL) at −78° C. was added commercially available N,N-dibenzylimine of glycine ethyl ester (25.0 g, 93.53 mmol) in THF (112 mL). The reaction mixture was warmed to 0° C., stirred for 40 minutes, and was then cooled back to −78° C. To this solution was added trans-1,4-dibromo-2-butene (20.0 g, 93.50 mmol). The mixture was stirred for 1 hour at 0° C. and was cooled back to −78° C. Potassium tert-butoxide (11.55 g, 102.9 mmol) was added and the mixture immediately warmed to 0° C. and was stirred one more hour before concentrating in vacuo. The crude product was dissolved in diethyl ether (530 mL), treated with 1N aqueous HCl (106 mL, 106 mmol), and the resulting biphasic mixture stirred for 3.5 hours at room temperature. The layers were separated and the aqueous layer was washed with diethyl ether (2×) and adjusted to a basic pH with a saturated aqueous NaHCO₃ solution. The solution was extracted with diethyl ether (3×) and the combined organic extract was washed with brine, dried (MgSO₄), filtered, and concentrated in vacuo to obtain the free amine. This material was treated with a 4N HCl solution in dioxane (100 mL, 400 mmol) and concentrated to provide (1R,2S)/(1S,2R) 1-amino-2-vinylcyclopropane carboxylic acid ethyl ester hydrochloride as a brown semi-solid (5.3 g, 34% yield) identical to the material obtained from procedure A, except for the presence of a small unidentified aromatic impurity (8%).

2. Resolution of (1R,2S)/(1S,2R)N-Boc-1-amino-2-vinylcyclopropane carboxylic acid ethyl ester

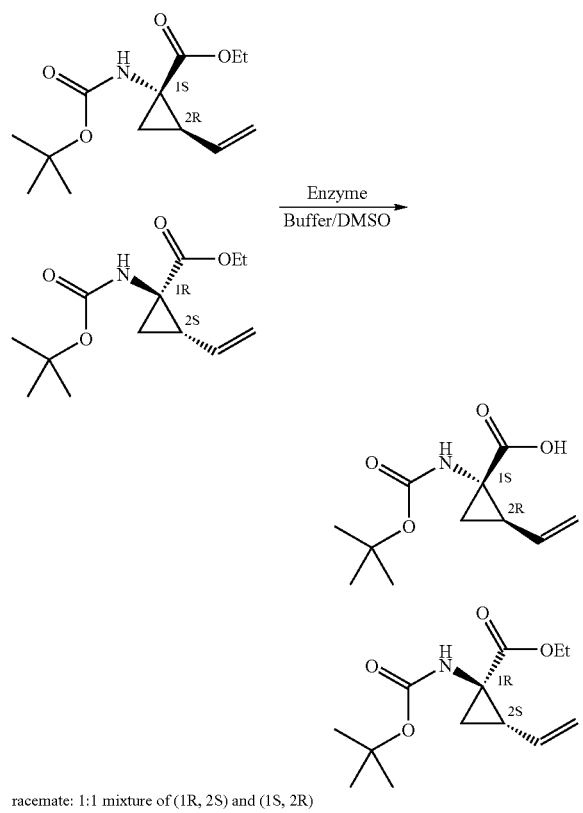

racemate: 1:1 mixture of (1R, 2S) and (1S, 2R)

Resolution A

To an aqueous solution of sodium phosphate buffer (0.1M, 4.25 L, pH 8) housed in a 12 Liter jacked reactor, maintained at 39° C., and stirred at 300 rpm, was added 511 grams of Alcalase 2.4 L (about 425 mL) (Novozymes North America Inc.). When the temperature of the mixture reached 39° C., the pH was adjusted to 8.0 by the addition of 50% NaOH in water. A solution of (1R,2S)/(1S,2R)N-Boc-1-amino-2-vinylcyclopropane carboxylic acid ethyl ester (85 g) in 850 mL of DMSO was then added over a period of 40 minutes. The reaction temperature was maintained at 40° C. for 24.5 hours during which time the pH of the mixture was adjusted to 8.0 at the 1.5 hour and 19.5 hour time points using 50% NaOH in water. After 24.5 hours, the enantio-excess of the ester was determined to be 97.2%, and the reaction was cooled to room temperature (26° C.) and stirred overnight (16 hours) at which time the enantio-excess of the ester was determined to be 100%. The pH of the reaction mixture was then adjusted to 8.5 with 50% NaOH and the resulting mixture was extracted with MTBE (2×2 L). The combined MTBE extract was washed with 5% NaHCO₃ (3×100 mL), water (3×100 mL), and then concentrated in vacuo to give the enantiomerically pure (1R,2S)N-Boc-1-amino-2-vinylcyclopropane carboxylic acid ethyl ester as light yellow solid (42.55 g; purity: 97% (210 nm, containing no acid; 100% enantiomeric excess ("ee").

The aqueous layer from the extraction process was adjusted to pH 2 with 50% H₂SO₄ and extracted with MTBE (2×2 L). The MTBE extract was washed with water (3×100 mL) and concentrated to give the acid as light yellow solid (42.74 g; purity: 99%@210 nm, containing no ester).

1R, 2S-ester 1S, 2R-acid

|  | ester | acid |
|---|---|---|
| High Resolution Mass Spec | (+) ESI, C₁₃H₂₂NO₄, [M + H]⁺, calcd. 256.1549, found 256.1542 | (−) ESI, C₁₁H₁₆NO₄, [M − H]⁻, calcd. 226.1079, found 226.1089 |

NMR observed chemical shift
Solvent: CDCl₃ (proton δ 7.24, C-13 δ 77.0)
Bruker DRX-500C: proton 500.032 MHz, carbon 125.746 MHz

| Position | Proton (pattern) ppm | C-13 ppm | Proton (pattern) ppm | C-13 ppm |
|---|---|---|---|---|
| 1 | — | 40.9 | — | 40.7 |
| 2 | 2.10 (q, J=9.0 Hz) | 34.1 | 2.17 (q, J=9.0 Hz) | 35.0 |
| 3a | 1.76 (br) | 23.2 | 1.79 (br) | 23.4 |
| 3b | 1.46 (br) | | 1.51, (br) | |
| 4 | — | 170.8 | — | 175.8 |
| 5 | 5.74 (ddd, J= 9.0, 10.0, 17.0 Hz) | 133.7 | 5.75 (m) | 133.4 |
| 6a | 5.25 (d, J=17.0 Hz) | 117.6 | 5.28 (d, J=17.0 Hz) | 118.1 |
| 6b | 5.08 (dd, J= 10.0, 1.5 Hz) | | 5.12 (d, J=10.5 Hz) | |
| 7 | — | 155.8 | — | 156.2 |
| 8 | — | 80.0 | — | 80.6 |
| 9 | 1.43 (s) | 28.3 | 1.43 (s) | 28.3 |
| 10 | 4.16 (m) | 61.3 | — | — |
| 11 | 1.23 (t, J=7.5 Hz) | 14.2 | — | — |

Resolution B

To 0.5 mL 100 mM Heps.Na buffer (pH 8.5) in a well of a 24 well plate (capacity: 10 mL/well), 0.1 mL of Savinase 16.0 L (protease from *Bacillus* clausii) (Novozymes North America Inc.) and a solution of (1R,2S)/(1S,2R)N-Boc-1-amino-2-vinylcyclopropane carboxylic acid ethyl ester (10 mg) in 0.1 mL of DMSO were added. The plate was sealed and incubated at 250 rpm at 40° C. After 18 hours, enantio-excess of the ester was determined to be 44.3% using the following procedure: 0.1 mL of the reaction mixture was removed and mixed well with 1 mL ethanol. After centrifugation, 10 microliter ("μL") of the supernatant was analyzed with the chiral HPLC. To the remaining reaction mixture, 0.1 mL of DMSO was added, and the plate was incubated for additional 3 days at 250 rpm at 40° C., after which 4 mL of ethanol was added to the well. After centrifugation, 10 μL of the supernatant was analyzed with the chiral HPLC and enantio-excess of the ester was determined to be 100%.

Resolution C

To 0.5 mL 100 mM Heps.Na buffer (pH 8.5) in a well of a 24 well plate (capacity: 10 mL/well), 0.1 mL of Esperase 8.0 L, (protease from *Bacillus halodurans*) (Novozymes North America Inc.) and a solution of (1R,2S)/(1S,2R) N-Boc-1-amino-2-vinylcyclopropane carboxylic acid ethyl ester (10 mg) in 0.1 mL of DMSO were added. The plate was sealed and incubated at 250 rpm at 40° C. After 18 hours, enantio-excess of the ester was determined to be 39.6% using the following procedure: 0.1 mL of the reaction mixture was removed and mixed well with 1 mL ethanol; after centrifugation, 10 μL of the supernatant was analyzed with the chiral HPLC. To the remaining reaction mixture, 0.1 mL of DMSO was added, and the plate was incubated for additional 3 days at 250 rpm at 40° C., after which 4 mL of ethanol was added to the well. After centrifugation, 10 μL of the supernatant was analyzed with the chiral HPLC and enantio-excess of the ester was determined to be 100%.

Samples analysis was carried out in the following manner:
1) Sample preparation: About 0.5 mL of the reaction mixture was mixed well with 10 volume of ethanol. After centrifugation, 10 μL of the supernatant was injected onto HPLC column.
2) Conversion Determination:
Column: YMC ODS A, 4.6×50 mm, S-5 μm
Solvent: A, 1 mM HCl in water; B, acetonitrile
Gradient: 30% B for 1 minute; 30% to 45% B over 0.5 minutes; 45% B for 1.5 minutes; 45% to 30% B over 0.5 minutes.
Flow rate: 2 mL/min
UV Detection: 210 nm
Retention time: acid, 1.2 minutes; ester, 2.8 minutes.
3) Enantio-Excess Determination for the Ester:
Column: CHIRACEL OD-RH, 4.6×150 mm, S-5 μm
Mobile phase: acetonitrile/50 mM $HClO_4$ in water (67/33)
Flow rate: 0.75 mL/minutes.
UV Detection: 210 nm.
Retention Time:
(1S,2R) 1-amino-2-vinylcyclopropane carboxylic acid 5.2 minutes;
(1R,2S)/(1S,2R)-1-amino-2-vinylcyclopropane carboxylic acid ethyl ester 18.5 minutes and 20.0 minutes;
(1R,2S) 1-amino-2-vinylcyclopropane carboxylic acid ethyl ester 18.5 minutes.

Resolution D

A solution of 0.3M sodium phosphate buffer (pH 8, 5 L) at 38° C. in a 20 L jacked reactor was stirred at 130 rpm and treated with 4 L of Alcalase 2.4 L (Novozymes North America Inc.) and 1 L of DI water. When the temperature of the mixture approached 38° C. the pH was adjusted to 7.8 with 10N NaOH. A solution of the racemic N-Boc-(1R,2S)/(1S,2R) 1-amino-2-vinylcyclopropane carboxylic acid ethyl ester (500 grams) in 5 L DMSO was added to the reactor over a period of 1 hour via addition funnel. The reaction temperature was adjusted to 48° C. and stirred for 21 hours, at which time the enantio-excess of the ester reached 99.3%. Heating was stopped at 24 hours and the reaction was slowly cooled to room temperature (about 25° C.) and stirred overnight. The pH of the reaction mixture was adjusted to 8.5 with 10N NaOH and the mixture was extracted with MTBE (2×4 L). The combined MTBE extracts were washed with 5% $NaHCO_3$ (3×400 mL) and water (3×400 mL), and concentrated to give enantiomerically pure (1R,2S)N-Boc-1-amino-2-vinylcyclopropane carboxylic acid ethyl ester as light yellow crystal (259 g; purity: 96.9%@210 nm, containing no acid; 100% ee).

Resolution E

To a solution of 10 L of 0.1M sodium phosphate buffer (pH 8) at 40° C. in a 20 L jacked reactor stirred at 360 rpm was added 1.5 L of Alcalase 2.4 L (Novozymes North America Inc.). When the temperature of the mixture approached 38° C., the pH was adjusted to 8.0 with 10N NaOH. A solution of (1R,2S)/(1S,2R) N-Boc-1-amino-2-vinylcyclopropane carboxylic acid ethyl ester (200 grams) in 2 L DMSO was added to the reactor over a period of 1 hour via addition funnel. The reaction temperature was then adjusted to 40° C. After 3 hours, pH was adjusted to 8.0 with 10N NaOH. After 21 hours, the reaction was cooled to 25° C. The pH of the reaction mixture was adjusted to 8.5 with 10N NaOH and the mixture was extracted with MTBE (2×5 L). The combined MTBE extract was washed with 5% $NaHCO_3$ (3×500 mL) and water (3×200 mL), and concentrated to provide 110 g of yellow oil. The oil was set at room temperature under house vacuum and provided enantiomerically pure (1R,2S)N-Boc-1-amino-2-vinylcyclopropane carboxylic acid ethyl ester as colorless long rod crystals (101 g; purity: 97.9%@210 nm, containing no acid; 100% ee).

The crystal structure of enantiomerically pure (1R,2S)N-Boc-1-amino-2-vinylcyclopropane carboxylic acid ethyl ester has been characterized by single crystal analysis (X-ray NB#: 52795-093, refcode: 634592N1). The absolute configuration is not established for lack of a known chiral center or heavier atom(s). A chain structure along the crystallographic a-axis is formed via intermolecular hydrogen bonding between the amide group and the carbonyl oxygen atom (N . . . O 3.159 Å).

Structure of N-Boc-(1R,2S)-1-amino-2-vinylcyclopropane Carboxylic Acid Ethyl Ester:

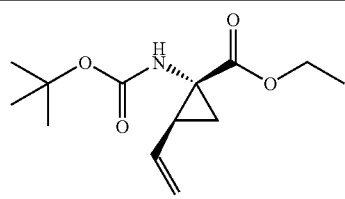

Crystal Data:
Chemical formula: $C_{13}H_{21}N_1O_4$
Crystal system: Orthorhombic
Space Group: $P2_12_12_1$
a = 5.2902(1) Å    α = 90°
b = 13.8946(2) Å   β = 90°
c = 19.9768(3) Å   γ = 90°
V = 1468.40(4) Å$^3$

43
-continued

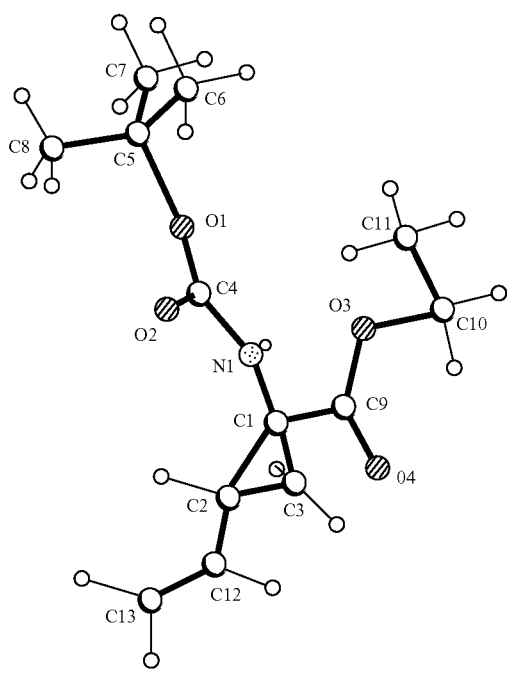

Experimental:
Crystallization
Crystal source: MTBE
Crystal description: Colorless rod
Crystal size (mm): 0.12 × 0.26 × 0.30
Data Collection
Temperature (K): 293
$\theta_{max}$ (°): 65.2 (Cu K$\alpha$)

Resolution F

A solution of 5 L of 0.2M sodium borate buffer (pH 9) at 45° C. in a 20 L jacked reactor stirred at 400 rpm was treated with 3 L of DI water and 4 L of Savinase 16 L, type EX (Novozymes North America Inc.). When the temperature of the mixture closed to 45° C., the pH was adjusted to 8.5 with 10N NaOH. A solution of (1R,2S)/(1S,2R)N-Boc-1-amino-2-vinylcyclopropane carboxylic acid ethyl ester (200 grams) in 2 L DMSO was added to the reactor over a period of 40 minutes via addition funnel. The reaction temperature was then adjusted to 48° C. After 2 hours, the pH was adjusted to pH 9.0 with 10N NaOH. At 18 hours, enantio-excess of the ester reached 72% and the pH was adjusted to 9.0 with 10N NaOH. At 24 hours the temperature was lowered to 35° C. At 42 hours the temperature was raised to 48° C. and the pH was adjusted to 9.0 with 10N NaOH. Heating was stopped at 48 hours and the reaction was slowly cooled down to room temperature (about 25° C.) and stirred overnight. At 66 hours, the pH of the reaction mixture was 8.6. The mixture was extracted with MTBE (2×4 L). The combined MTBE extracts were washed with 5% NaHCO$_3$ (6×300 mL) and water (3×300 mL) and concentrated to give enantiomerically pure (1R,2S)N-Boc-1-amino-2-vinylcyclopropane carboxylic acid ethyl ester as light yellow crystals (101A g; purity: 95.9% (210 nm, containing no acid; 98.6% ee).

44

3. Preparation of Chiral (1R,2S)-1-amino-2-vinylcyclopropane carboxylic acid ethyl ester hydrochloride

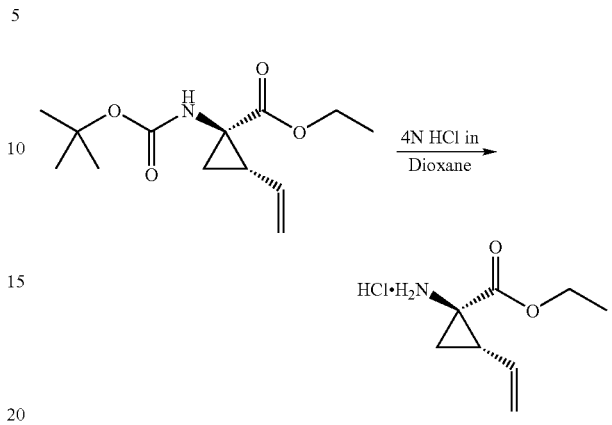

(1R,2S)N-Boc-1-amino-2-vinylcyclopropanecarboxylic acid ethyl ester (8.5 g, 33.3 mmol) was stirred under a nitrogen atmosphere with 200 mL of 4N HCl/dioxane (Aldrich) at room temperature for 3 hours. The solvent was removed under reduced pressure keeping the temperature below 40° C. This gave 6.57 g (~100%) of (1R,2S)-1-amino-2-vinylcyclopropanecarboxylic acid ethyl ester hydrochloride as a light tan solid. $^1$H NMR (300 MHz, CD$_3$OD) δ 1.31 (t, J=7.0 Hz, 3H), 1.69-1.82 (m, 2H), 2.38 (q, J=8.8 Hz, 1H), 4.29 (q, J=7.0 Hz, 2H), 5.22 (d, J=10.3 Hz, 1H), 5.40 (d, J=17.2 Hz, 1H), 5.69-5.81 (m, 1H). MS m/z 156 (M$^+$+1).

4. Preparation of N-Boc-(1R,2S)-1-amino-2-cyclopropylcyclopropane carboxylic acid ethyl ester

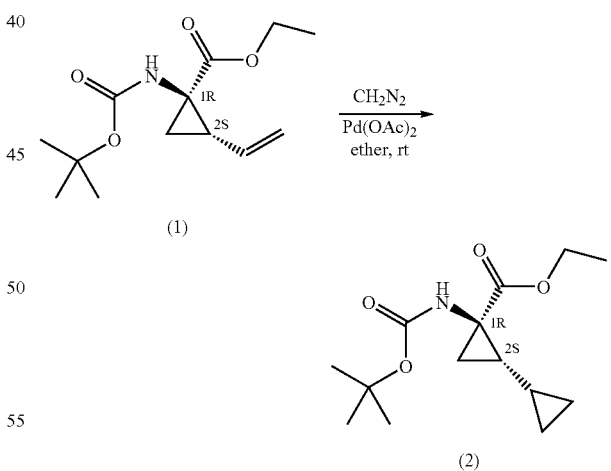

A solution of N-Boc-(1R,2S)-1-amino-2-vinylcyclopropane carboxylic acid (255 mg, 1.0 mmol) in diethyl ether (10 mL) was treated with palladium acetate (5 mg, 0.022 mmol). The orange/red solution was placed under a nitrogen atmosphere. An excess of diazomethane in diethyl ether was added dropwise over the course of 1 hour. The resulting solution was stirred at room temperature for 18 hours. The excess diazomethane was removed using a stream of nitrogen and the resulting solution was concentrated by rotary evaporation to give the crude product. Flash chromatography (10% ethyl acetate/hexane) provided 210 mg (78%) of (1R,2S)—N-Boc-1-amino-2-cyclopropylcyclopropane carboxylic acid ethyl ester as a colorless oil. LC-MS (retention time: 2.13, similar to method A except: gradient time 3 minutes, Xterra MS C18 S7 3.0×50 mm column), MS m/e 270 (M⁺+1).

5. 1-tert-Butoxycarbonylaminocyclopropane carboxylic acid is Commercially Available

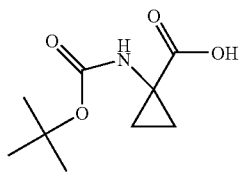

6. Preparation of 1-aminocyclobutanecarboxylic acid methyl ester-hydrochloride

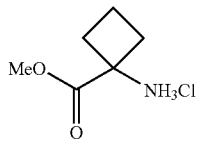

1-Aminocyclobutanecarboxylic acid (100 mg, 0.869 mmol) (Tocris) was dissolved in 10 mL of methanol. HCl gas was bubbled in for 2 hours. The reaction mixture was stirred for 18 hours, and then concentrated in vacuo to give 144 mg of a yellow oil. Trituration with 10 mL of diethyl ether provided 100 mg of the desired product as a white solid. $^1$H NMR (CDCl$_3$) δ 2.10-2.25 (m, 1H), 2.28-2.42 (m, 1H), 2.64-2.82 (m, 4H), 3.87 (s, 3H), 9.21 (br s, 3H).

7. Preparation of (1R,2R)/(1S,2S) 1-amino-2-ethylcyclopropanecarboxylic acid tert-Butyl ester (Racemic Mixture)

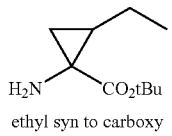

ethyl syn to carboxy

Step 1: Preparation of
2-ethylcyclopropane-1,1-dicarboxylic acid
di-tert-butyl ester, Shown Below

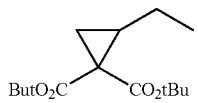

To a suspension of benzyltriethylammonium chloride (21.0 g, 92.2 mmol) in a 50% aqueous NaOH solution (92.4 g in 185 mL H$_2$O) was added 1,2-dibromobutane (30.0 g, 138.9 mmol) and di-tert-butylmalonate (20.0 g, 92.5 mmol). The reaction mixture was vigorously stirred for 18 hours at room temperature and treated with a mixture of ice and water. The crude product was extracted with dichloromethane (3×) and sequentially washed with water (3×), and brine. The organic extracts were combined, dried (MgSO$_4$), filtered, and concentrated in vacuo. The resulting residue was purified by flash column chromatography (100 g SiO$_2$, 3% diethyl ether in hexane) to provide the desired product (18.3 g, 67.8 mmol, 73% yield) which was used directly in the next reaction.

Step 2: Preparation of racemic
2-Ethylcyclopropane-1,1-dicarboxylic acid tert-butyl
ester, Shown Below

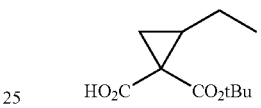

The product of Step 1 (18.3 g, 67.8 mmol) was added to a suspension of potassium tert-butoxide (33.55 g, 299.0 mmol) in dry diethyl ether (500 mL) at 0° C., treated with H$_2$O (1.35 mL, 75.0 mmol), and was vigorously stirred overnight at room temperature. The reaction mixture was poured in a mixture of ice and water and washed with diethyl ether (3×). The aqueous layer was adjusted to acidic pH with a 10% aqueous citric acid solution at 0° C. and extracted with ethyl acetate (3×). The combined organic layers were washed with water (2×), brine, dried (MgSO$_4$), filtered, and concentrated in vacuo to provide the desired product as a pale yellow oil (10 g, 46.8 mmol, 69% yield).

Step 3: Preparation of (1R,2R)/(1S,2S) 2-ethyl-1-(2-trimethylsilanylethoxycarbonylamino)cyclopropane-carboxylic acid tert-butyl ester, Shown Below

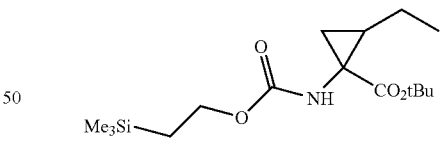

To a suspension of the product of Step 2 (10 g, 46.8 mmol) and 3 g of freshly activated 4 Å molecular sieves in dry benzene (160 mL) was added triethylamine (7.50 mL, 53.8 mmol) and DPPA (11 mL, 10.21 mmol). The reaction mixture was heated to reflux for 3.5 hours, treated with 2-trimethyl-silyl-ethanol (13.5 mL, 94.2 mmol), and heated to reflux overnight. The reaction mixture was filtered, diluted with diethyl ether, washed sequentially with 10% aqueous citric acid solution, water, saturated aqueous NaHCO$_3$, water (2×), and brine (2×), dried (MgSO$_4$), filtered, and concentrated in vacuo. The residue was suspended with 10 g of Aldrich poly-isocyanate scavenger resin in 120 mL of dichloromethane, stirred at room temperature overnight, and filtered to provide the desired product (8 g, 24.3 mmol; 52%) as a pale yellow oil: ¹H NMR (CDCl₃) δ 0.03 (s, 9H), 0.97 (m, 5H), 1.20 (br m, 1H), 1.45 (s, 9H), 1.40-1.70 (m, 4H), 4.16 (m, 2H), 5.30 (br s, 1H).

Step 4: Preparation of (1R,2R)/(1S,2S) 1-amino-2-ethylcyclopropanecarboxylic acid tert-butyl ester (Racemic Mixture), Shown Below

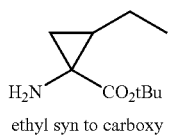

ethyl syn to carboxy

To the product of Step 3 (3 g, 9 mmol) was added a 1.0M TBAF solution in THF (9.3 mL, 9.3 mmol). The mixture was heated to reflux for 1.5 hours, cooled to room temperature, and diluted with 500 mL of ethyl acetate. The solution was successively washed with water (2×100 mL) and brine (2×100 mL), dried (MgSO₄), filtered, and concentrated in vacuo to provide the desired product.

II. Preparation of P1' Intermediates

1. Preparation of Cyclopropylsulfonamide

Method 1 (of 2):

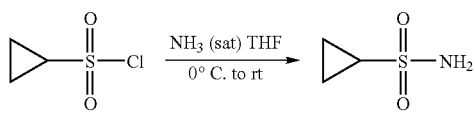

To a solution of 100 mL of THF cooled to 0° C. was bubbled in gaseous ammonia until saturation was reached. To this solution was added a solution of 5 g (28.45 mmol) of cyclopropylsulfonyl chloride (purchased from Array Biopharma) in 50 mL of THF. The solution was warmed to room temperature overnight and stirred one additional day. The mixture was concentrated until 1-2 mL of solvent remained and poured onto a 30 g plug of SiO₂ (eluted with 30% to 60% ethyl acetate/hexanes) to provide 3.45 g (100%) of cyclopropylsulfonamide as a white solid. ¹H NMR (methanol-d₄) δ 0.94-1.07 (m, 4H), 2.52-2.60 (m, 1H); ¹³C NMR (methanol-d₄) δ 5.92, 33.01.

Method 2 (of 2):

Step 1: Preparation of N-tert-butyl-(3-chloro)propylsulfonamide

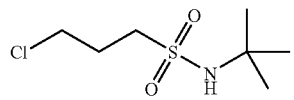

tert-Butylamine (3.0 mol, 315.3 mL) was dissolved in THF (2.5 L). The solution was cooled to −20° C. and treated slowly with 3-chloropropanesulfonyl chloride (1.5 mol, 182.4 mL). The reaction mixture was warmed to room temperature and stirred for 24 hours. The mixture was filtered, and the filtrate was concentrated in vacuo. The concentrate was dissolved in dichloromethane (2.0 L), washed with 1N HCl (1.0 L), water (1.0 L), brine (1.0 L), dried over Na₂SO₄, filtered, and concentrated in vacuo to give a slightly yellow solid, which was crystallized from hexane to provide the desired product as a white solid (316.0 g, 99%). ¹H NMR (CDCl₃) δ 1.38 (s, 9H), 2.30-2.27 (m, 2H), 3.22 (t, J=7.35 Hz, 2H), 3.68 (t, J=6.2 Hz, 2H), 4.35 (br, 1H).

Step 2: Preparation of Cyclopropanesulfonic Acid Tert-Butylamide

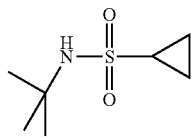

To a solution of N-tert-butyl-(3-chloro)propylsulfonamide (2.14 g, 10.0 mmol) in THF (100 mL) was added n-butyllithium (2.5M in hexane, 8.0 mL, 20.0 mmol) at −78° C. The reaction mixture was warmed to room temperature over a period of 1 hour and concentrated in vacuo. The concentrate was partitioned between ethyl acetate and water (200 mL, 200 mL). The organic phase was washed with brine, dried over Na₂SO₄, filtered and concentrated in vacuo. The concentrate was recrystallized from hexane to provide the desired product as a white solid (1.0 g, 56%). ¹H NMR (CDCl₃) δ 0.98-1.00 (m, 2H), 1.18-1.19 (m, 2H), 1.39 (s, 9H), 2.48-2.51 (m, 1H), 4.19 (br, 1H).

Step 3: Preparation of Cyclopropylsulfonamide

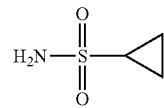

A solution of cyclopropanesulfonic acid tert-butylamide (110.0 g, 0.62 mol) in TFA (500 mL) was stirred at room temperature for 16 hours and concentrated in vacuo. The residue was recrystallized from ethyl acetate/hexane (60 mL/240 mL) to provide the desired product as a white solid (68.5 g, 91%). ¹H NMR (DMSO-d₆) δ 0.84-0.88 (m, 2H), 0.95-0.98 (m, 2H), 2.41-2.58 (m, 1H), 6.56 (br, 2H).

2. Preparation of Cl-Substituted Cyclopropylsulfonamides

2a. Preparation of N-tert-butyl-(1-methyl)cyclopropyl-sulfonamide

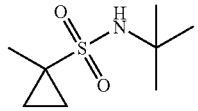

Step 1: Preparation of N-tert-butyl-(3-chloro)propylsulfonamide

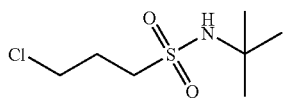

Prepared as described above.

Step 2: Preparation of N-tert-butyl-(1-methyl)cyclopropyl-sulfonamide

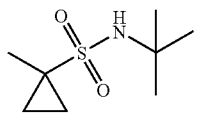

A solution of N-tert-butyl-(3-chloro)propylsulfonamide (4.3 g, 20 mmol) was dissolved in dry THF (100 mL) and cooled to −78° C. To this solution was added n-butyllithium (17.6 mL, 44 mmol, 2.5M in hexane) slowly. The dry ice bath was removed and the reaction mixture was warmed to room temperature over a period of 1.5 hours. This mixture was cooled to −78° C. and a solution of n-butyllithium (20 mmol, 8 mL, 2.5M in hexane) was added. The reaction mixture was warmed to room temperature, cooled to −78° C. over a period of 2 hours, and treated with a neat solution of methyl iodide (5.68 g, 40 mmol). The reaction mixture was warmed to room temperature overnight, then quenched with saturated NH$_4$Cl (100 mL) at room temperature and extracted with ethyl acetate (100 mL). The organic phase was washed with brine (100 mL), dried (MgSO$_4$), filtered, and concentrated in vacuo to provide a yellow oil which was crystallized from hexane to provide the desired product as a slightly yellow solid (3.1 g, 81%): $^1$H NMR (CDCl$_3$) δ 0.79 (m, 2H), 1.36 (s, 9H), 1.52 (m, 2H), 1.62 (s, 3H), 4.10 (br s, 1H).

Step 3: Preparation of 1-methylcyclopropylsulfonamide

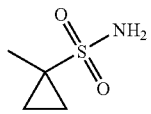

A solution of N-tert-butyl-(1-methyl)cyclopropylsulfonamide (1.91 g, 10 mmol) was dissolved in TFA (30 mL), and the reaction mixture stirred at room temperature for 16 hours. The solvent was removed in vacuo to provide a yellow oil which was crystallized from ethyl acetate/hexane (1:4, 40 mL) to provide the desired product as a white solid (1.25 g, 96%): $^1$H NMR (CDCl$_3$) δ 0.84 (m, 2H), 1.41 (m, 2H), 1.58 (s, 3H), 4.65 (br s, 2H). Anal. Calcd. For C$_4$H$_9$NO$_2$S: C, 35.54; H, 6.71; N, 10.36. Found: C, 35.67; H, 6.80; N, 10.40.

2b. Preparation of 1-Benzylcyclopropylsulfonamide

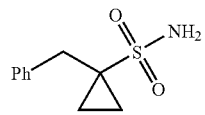

Step 1: Preparation of N-tert-butyl-(1-benzyl)cyclopropyl-sulfonamide

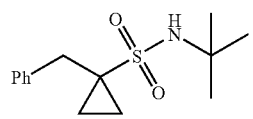

This compound was obtained in 60% yield using the procedure described for the synthesis of N-tert-butyl-(1-methyl)cyclopropylsulfonamide using 1.05 equivalents of benzyl bromide. Trituration with 10% ethyl acetate in hexane provided the desired product: $^1$H NMR (CDCl$_3$) δ 0.92 (m, 2H), 1.36 (m, 2H), 1.43 (s, 9H), 3.25 (s, 2H), 4.62 (br s, 1H), 7.29-7.36 (m, 5H).

Step 2: Preparation of 1-benzylcyclopropylsulfonamide

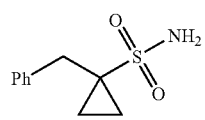

This compound was obtained in 66% yield from N-tert-butyl(1-benzyl)cyclopropylsulfonamide using the procedure described for the synthesis of 1-methylcyclopropylsulfonamide, followed by recrystallization from the minimum amount of 10% ethyl acetate in hexane: $^1$H NMR (CDCl$_3$) δ 0.90 (m, 2H), 1.42 (m, 2H), 3.25 (s, 2H), 4.05 (s, 2H), 7.29 (m, 3H), 7.34 (m, 2H); $^{13}$C NMR (CDCl$_3$) δ 11.1, 36.8, 41.9, 127.4, 128.8, 129.9, 136.5.

2c. Preparation of 1-propylcyclopropylsulfonamide

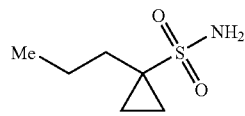

This compound was prepared using the procedure described for the preparation of 1-methylcyclopropylsulfonamide substituting propyl halide for methyl iodide in the second step of this process.

2d. Preparation of 1-allylcyclopropylsulfonamide

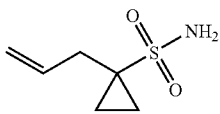

Step 1: Preparation of
N-tert-butyl-(1-allyl)cyclopropylsulfonamide

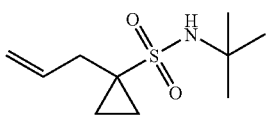

This compound was obtained in 97% yield according to the procedure described in the synthesis of N-tert-butyl-(1-methyl)cyclopropylsulfonamide using 1.25 equivalents of allyl bromide as the electrophile. The compound was used in the next reaction without further purification: $^1$H NMR (CDCl$_3$) δ 0.83 (m, 2H), 1.34 (s, 9H), 1.37 (m, 2H), 2.64 (d, J=7.3 Hz, 2H), 4.25 (br s, 1H), 5.07-5.10 (m, 2H), 6.70-6.85 (m, 1H).

Step 2: Preparation of 1-allylcyclopropylsulfonamide

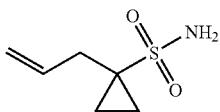

This compound was obtained in 40% yield from N-tert-butyl-(1-allyl)cyclopropylsulfonamide according to the procedure described in the synthesis of 1-methylcyclopropylsulfonamide. The compound was purified by column chromatography over SiO$_2$ using 2% methanol in dichloromethane as the eluent: $^1$H NMR (CDCl$_3$) δ 0.88 (m, 2H), 1.37 (m, 2H), 2.66 (d, J=7.0 Hz, 2H), 4.80 (s, 2H), 5.16 (m, 2H), 5.82 (m, 1H); $^{13}$C NMR (CDCl$_3$) δ 11.2, 35.6, 40.7, 119.0, 133.6.

2e. Preparation of
1-(1-cyclohexenyl)cyclopropyl-sulfonamide

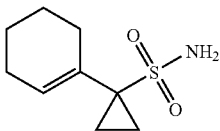

Step 1: Preparation of N-tert-butyl-[1-(1-hydroxy)cyclohexyl]-cyclopropylsulfonamide

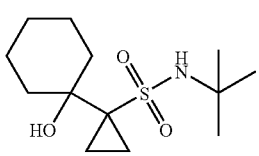

This compound was obtained in 84% yield using the procedure described for the synthesis of N-tert-butyl-(1-methyl)cyclopropylsulfonamide using 1.30 equivalents of cyclohexanone. Recrystallization from the minimum amount of 20% ethyl acetate in hexane provided the desired product: $^1$H NMR (CDCl$_3$) δ 1.05 (m, 4H), 1.26 (m, 2H), 1.37 (s, 9H), 1.57-1.59 (m, 6H), 1.97 (m, 2H), 2.87 (br s, 1H), 4.55 (br s, 1H).

Step 2: Preparation of
1-(1-cyclohexenyl)cyclopropyl-sulfonamide

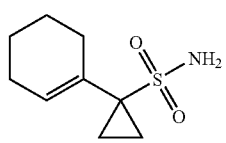

This compound, 1-(1-cyclohexenyl)cyclopropylsulfonamide was obtained in 85% yield from N-tert-butyl-[1-(1-hydroxy)cyclohexyl]cyclopropylsulfonamide using the procedure described for the synthesis of 1-methylcyclopropylsulfonamide. Recrystallization from the minimum amount of ethyl acetate and hexane provided the desired product: $^1$H NMR (DMSO-d$_6$) δ 0.82 (m, 2H), 1.28 (m, 2H), 1.51 (m, 2H), 1.55 (m, 2H), 2.01 (s, 2H), 2.16 (s, 2H), 5.89 (s, 1H), 6.46 (s, 2H); $^{13}$C NMR (DMSO-d$_6$) δ 11.6, 21.5, 22.3, 25.0, 27.2, 46.9, 131.6, 132.2; LR-MS (ESI): 200 (M$^+$–1).

2f. Preparation of 1-benzoylcyclo-propylsulfonamide

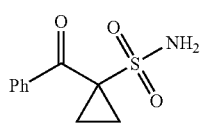

Step 1: Preparation of
N-tert-butyl-(1-benzoyl)cyclopropyl-sulfonamide

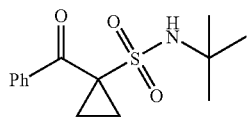

This compound was obtained in 66% yield using the procedure described for the synthesis of N-tert-butyl-(1-methyl)cyclopropylsulfonamide using 1.2 equivalents of methyl benzoate as the electrophile. The crude product was purified by column chromatography over SiO$_2$ using 30% to 100% dichloromethane in hexane: $^1$H NMR (CDCl$_3$) δ 1.31 (s, 9H), 1.52 (m, 2H), 1.81 (m, 2H), 4.16 (br s, 1H), 7.46 (m, 2H), 7.57 (m, 1H), 8.05 (d, J=8.5 Hz, 2H).

Step 2: Preparation of 1-benzoylcyclo-propylsulfonamide

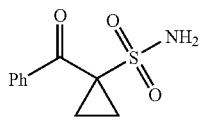

This compound was obtained in 87% yield from N-tert-butyl(1-benzoyl)cyclopropylsulfonamide using the procedure described for the synthesis of 1-methylcyclopropylsulfonamide. Recrystallization from the minimum amount of ethyl acetate in hexane provided the desired product: $^1$H NMR (DMSO-$d_6$) δ 1.39 (m, 2H), 1.61 (m, 2H), 7.22 (s, 2H), 7.53 (t, J=7.6 Hz, 2H), 7.65 (t, J=7.6 Hz, 1H), 8.06 (d, J=8.2 Hz, 2H); $^{13}$C NMR (DMSO-$d_6$) δ 12.3, 48.4, 128.1, 130.0, 133.4, 135.3, 192.0.

2g. Preparation of N-tert-butyl-(1-phenylaminocarboxy)-cyclopropylsulfonamide

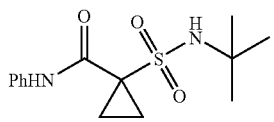

This compound was obtained in 42% yield using the procedure described for the synthesis of N-tert-butyl-(1-methyl)cyclopropylsulfonamide using 1 equivalent of phenylisocyanate. Recrystallization from the minimum amount of ethyl acetate in hexane provided the desired product. $^1$H NMR (CDCl$_3$) δ 1.38 (s, 9H), 1.67-1.71 (m, 4H), 4.30 (br s, 1H), 7.10 (t, J=7.5 Hz, 1H), 7.34 (t, J=7.5 Hz, 2H), 7.53 (t, J=7.5 Hz, 2H).

3. Preparation of Cl-Substituted Cyclopropanesulfonamides: The Use of an N-Boc Protecting Group

3a. Preparation of Cyclopropylsulfonylamine Tert-Butyl Carbamate, a Key Intermediate in the Preparation of Cl-Substituted Cyclopropylsulfonamides

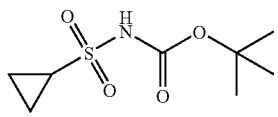

Step 1: Preparation of 3-chloropropylsulfonamide

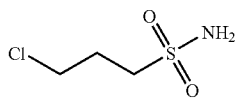

A solution of 3-chloropropanesulfonyl chloride (55 g, 310.7 mmol) was dissolved in THF (200 mL) and added dropwise over 30 minutes to a solution of NH$_4$OH (200 mL) at 0° C. The reaction mixture was warmed to room temperature, stirred 1 hour, and the aqueous layer extracted with dichloromethane (4×500 mL). The combined extracts were washed with 1N HCl (150 mL), water (150 mL), dried over MgSO$_4$, filtered, and concentrated in vacuo. The crude solid was recrystallized from the minimum amount of dichloromethane in hexanes to provide the desired product as a white solid (45.3 g, 93%). $^1$H NMR (CDCl$_3$) δ 2.34 (m, 2H), 3.32 (t, J=7.3 Hz, 2H), 3.70 (t, J=6.2 Hz, 2H), 4.83 (s, 2H); $^{13}$C NMR (CDCl$_3$) δ 27.10, 42.63, 52.57.

Step 2: Preparation of 3-chloropropylsulfonylamine tert-butylcarbamate

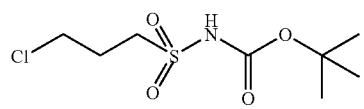

A solution of 3-chloropropylsulfonamide (30.2 g, 191.5 mmol), triethylamine (30.2 mL, 217.0 mmol), and 4-DMAP (2.40 g, 19.6 mmol) in dichloromethane (350 mL) at 0° C. was treated dropwise with a solution of di-tert-butyldicarbonate (47.2 g, 216.9 mmol) in dichloromethane (250 mL) over 30 minutes. The reaction mixture was warmed to room temperature, stirred an additional 3 hours, and was washed with 1N HCl (300 mL), water (300 mL), and brine (300 mL), dried over MgSO$_4$, filtered, and concentrated in vacuo to provide the crude product. This material was triturated with 70 mL of 5% dichloromethane in hexanes to provide the desired product as an off-white solid (47.2 g, 96%): $^1$H NMR (CDCl$_3$) δ 1.51 (s, 9H), 2.33 (m, 2H), 3.60 (t, J=7.3 Hz, 2H), 3.68 (t, J=6.21 Hz, 2H); $^{13}$C NMR (CDCl$_3$) δ 26.50, 27.95, 42.37, 50.40, 84.76, 149.53.

Step 3: Preparation of Cyclopropylsulfonylamine Tert-Butyl Carbamate

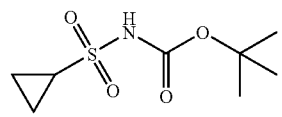

A solution of n-butyllithium (74.7 mL, 119.5 mmol, 1.6M in hexane) was dissolved in dry THF (105 mL) and cooled to −78° C. under an argon atmosphere. To this solution was added a solution of 3-chloropropylsulfonylamine tert-butylcarbamate (14 g, 54.3 mmol) in dry THF (105 mL) dropwise over 20-30 minutes. The dry ice bath was removed and the reaction mixture was allowed to warm to room temperature over a period of 2 hours. The reaction mixture was quenched with glacial acetic acid (3.4 mL), concentrated in vacuo, and partitioned between dichloromethane (100 mL) and water (100 mL). The organic phase was washed with brine (100 mL), dried (MgSO$_4$), filtered, and concentrated in vacuo to provide the desired product as a waxy off-white solid (12.08 g, 100%): $^1$H NMR (CDCl$_3$) δ 1.10 (m, 2H), 1.34 (m, 2H), 1.50 (s, 9H), 2.88 (m, 1H), 7.43 (s, 1H). $^{13}$C NMR (CDCl$_3$) δ 6.21, 28.00, 31.13, 84.07, 149.82.

3b. Preparation of 1-methoxy-methylcyclopropylsulfonamide

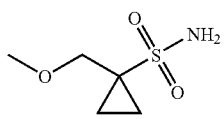

Step 1: Preparation of 1-methoxymethylcyclopropylsulfonylamine tert-butylcarbamate

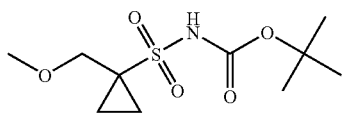

To a solution of cyclopropylsulfonylamine tert-butyl carbamate (1.0 g, 4.5 mmol) dissolved in THF (30 mL) cooled to −78° C. was added n-butyllithium (6.4 mL, 10.2 mmol, 1.6M in hexane) and the reaction mixture was stirred for 1 hour. To this solution was added a neat solution of chloromethyl methyl ether (0.40 mL, 5.24 mmol), and the mixture was slowly warmed to room temperature overnight. The solution pH was adjusted to 3 using 1N aqueous HCl and was then extracted with ethyl acetate (4×50 mL portions). The combined extracts were dried (MgSO$_4$), filtered, and concentrated to provide the desired product as a waxy solid (1.20 g, 100%) which was taken directly into the next reaction without further purification: $^1$H NMR (CDCl$_3$) δ 1.03 (m, 2H), 1.52 (s, 9H), 1.66 (m, 2H), 3.38 (s, 3H), 3.68 (s, 2H), 7.54 (s, 1H); $^{13}$C NMR (CDCl$_3$) δ 11.37, 28.29, 40.38, 58.94, 73.43, 83.61, 149.57.

Step 2: Preparation of 1-methoxymethylcyclopropysulfonamide

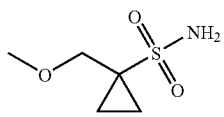

A solution of 1-methoxymethylcyclopropylsulfonylamine tert-butylcarbamate (1.14 g, 4.30 mmol) was dissolved in a solution of 50% TFA/dichloromethane (30 mL) and was stirred at room temperature for 16 hours. The solvent was removed in vacuo and the residue purified by column chromatography over 80 g of SiO$_2$ (eluting with 0% to 60% ethyl acetate/hexanes) to provide the desired product as a white solid (0.55 g, 77% overall over two steps): $^1$H NMR (CDCl$_3$) δ 0.95 (m, 2H), 1.44 (m, 2H), 3.36 (s, 3H), 3.65 (s, 2H), 4.85 (s, 2H); $^{13}$C NMR (CDCl$_3$) δ 11.17, 40.87, 59.23, 74.80; LRMS m/z 183 (M$^+$+NH$_4$).

3c. Preparation of 1-cyclopropylmethylcyclopropanesulfonamide

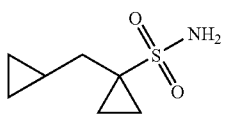

Step 1: Preparation of 1-cyclopropylmethylcyclopropanesulfonylamine tert-butylcarbamate

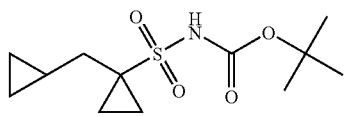

1-Cyclopropylmethylcyclopropylsulfonylamine tert-butylcarbamate was obtained in 92% yield according to the procedure described in the synthesis of 1-methoxymethylcyclopropylsulfonylamine tert-butylcarbamate using 1.10 equivalents of cyclopropylmethyl bromide as the electrophile. The compound was taken directly into the next reaction without purification: $^1$H NMR (CDCl$_3$) δ 0.10 (m, 2H), 0.51 (m, 2H), 0.67 (m, 1H), 1.10 (m, 2H), 1.49 (s, 9H), 1.62 (m, 2H), 1.87 (d, J=7.0 Hz, 2H).

Step 2: Preparation of 1-cyclopropylmethylcyclopropylsulfonamide

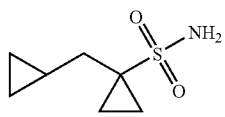

This compound was obtained in 65% yield from 1-cyclopropylmethylcyclopropylsulfonylamine tert-butylcarbamate according to the procedure described for the synthesis of 1-methoxymethylcyclopropylsulfonamide. The compound was purified by column chromotography over SiO$_2$ using 0% to 60% ethyl acetate in hexanes as the eluent: $^1$H NMR (CDCl$_3$) δ 0.15 (m, 2H), 0.51 (m, 2H), 1.01 (m, 2H), 1.34 (m, 3H), 1.86 (d, J=7.0 Hz, 2H), 4.83 (s, 2H); $^{13}$C NMR (CDCl$_3$) δ 4.65, 7.74, 11.26, 35.62, 41.21; LRMS m/z 193 (M$^+$+NH$_4$).

3d. Preparation of 1-propylcarbamoylcyclopropanesulfonamide

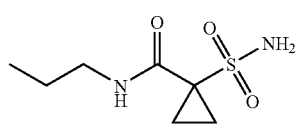

Step 1: Preparation of 1-propylcarbamoylcyclopropanesulfonamide tert-butylcarbamate

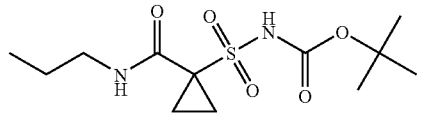

This compound was obtained in a crude 100% yield according to the procedure described for the synthesis of 1-methoxymethylcyclopropylsulfonylamine tert-butyl-carbamate using 1.10 equivalents of n-propyl isocyanate as the electrophile. The compound was taken directly into the next reaction without purification: $^1$H NMR (CDCl$_3$) δ 0.10 (m, 2H), 0.51 (m, 2H), 0.67 (m, 1H), 1.10 (m, 2H), 1.49 (s, 9H), 1.62 (m, 2H), 1.87 (d, J=7.0 Hz, 2H).

Step 2: Preparation of 1-propylcarbamoylcyclopropane-sulfonamide

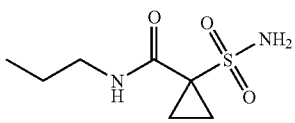

This compound was obtained in an optimized 50% yield from 1-propylcarbamoylcyclopropanesulfonamide tert-butylcarbamate according to the procedure described for the synthesis of 1-methoxymethylcyclopropylsulfonamide, except that no chromatography was used as the material was recrystallized from the minimum amount of dichloromethane/hexanes: $^1$H NMR (CDCl$_3$) δ 0.15 (m, 2H), 0.51 (m, 2H), 1.01 (m, 2H), 1.34 (m, 3H), 1.86 (d, J=7.0 Hz, 2H), 4.83 (s, 2H); $^{13}$C NMR (CDCl$_3$) δ 4.65, 7.74, 11.26, 35.62, 41.21; LRMS m/z 193 (M$^+$+NH$_4$).

3e. Preparation of 1-(3,5-dimethylisoxazol-4-yl)carbamoylcyclopropanesulfonamide

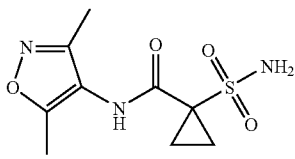

Step 1: Preparation of 1-(3,5-dimethylisoxazol-4-yl)carbamoylcyclopropanesulfonamide tert-butylcarbamate

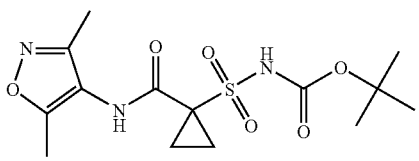

This compound was obtained in a crude 100% yield according to the procedure described for the synthesis of 1-methoxymethylcyclopropylsulfonylamine tert-butylcarbamate except that 1.20 equivalents of 3,5-dimethylisoxazole-4-isocyanate was used as the electrophile. The compound was taken directly into the next reaction without purification.

Step 2: Preparation of 1-(3,5-dimethylisoxazol-4-yl)carbamoylcyclopropanesulfonamide

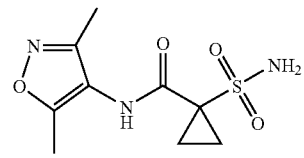

This compound was obtained in 50% yield (580 mg) from 1.62 g (4.52 mmol) of 1-(3,5-dimethylisoxazol-4-yl)carbamoylcyclopropanesulfonamide tert-butylcarbamate using 30 mL (120 mmol) of 4N HCl/dioxanes, stirring overnight, concentration and chromatography over a Biotage 40M column (eluting with 0% to 5% methanol/dichloromethane: $^1$H NMR (methanol-d$_4$) δ 1.57 (m, 2H), 1.61 (m 2H), 2.15 (s, 3H), 2.30 (s, 3H), 4.84 (s, 3H); $^{13}$C NMR (methanol-d$_4$) δ 9.65, 10.94, 15.01, 46.11, 114.82, 159.45, 165.55, 168.15; LRMS m/z 260 (M$^+$+H).

4. Preparation of Cycloalkylsulfonamides from Cyloalkylbromides

4a. Preparation of Cyclobutylsulfonamide from Cylobutyl Bromide

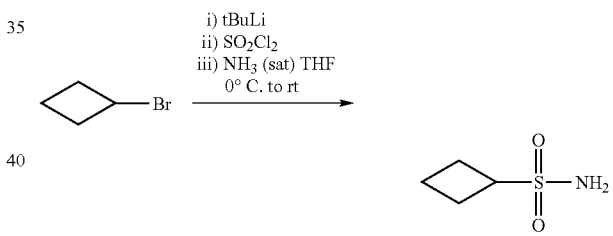

To a solution of 5.0 g (37.0 mmol) of cyclobutyl bromide in 30 mL of anhydrous diethyl ether (diethyl ether) cooled to −78° C. was added 44 mL (74.8 mmol) of 1.7M tert-butyllithium in pentanes. The solution was slowly warmed to −35° C. over 1.5 hours. This mixture was cannulated slowly into a solution of 5.0 g (37.0 mmol) of freshly distilled sulfuryl chloride in 100 mL of hexanes cooled to −40° C., warmed to 0° C. over 1 hour and carefully concentrated in vacuo. This mixture was redissolved in diethyl ether, washed once with some ice-cold water, dried (MgSO$_4$), filtered, and concentrated carefully. This mixture was redissolved in 20 mL of THF, added dropwise to 500 mL of saturated NH$_3$ in THF, and was allowed to stir overnight. The mixture was concentrated in vacuo to a crude yellow solid and was recrystallized from the minimum amount of dichloromethane in hexanes with 1-2 drops of methanol to afford 1.90 g (38%) of cyclobutylsulfonamide as a white solid. $^1$H NMR (CDCl$_3$) δ 1.95-2.06 (m, 2H), 2.30-2.54 (m, 4H), 3.86 (p, J=8 Hz, 1H), 4.75 (brs, 2H); $^{13}$C NMR (CDCl$_3$) δ 16.43, 23.93, 56.29. HRMS m/z (M-H)$^−$ calcd for C$_4$H$_8$NSO$_2$: 134.0276. found 134.0282.

4b. Preparation of Cyclopentyl Sulfonamide

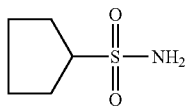

A solution of 18.5 mL (37.0 mmol) of 2M cyclopentylmagnesium chloride in ether was added dropwise to a solution of 3.0 mL (37.0 mmol) freshly distilled sulfuryl chloride (obtained from Aldrich) in 100 mL of hexanes cooled to −78° C. The mixture was warmed to 0° C. over 1 hour and was then carefully concentrated in vacuo. This mixture was redissolved in diethyl ether (200 mL), washed once with some ice-cold water (200 mL), dried (MgSO$_4$), filtered, and concentrated carefully. This mixture was redissolved in 35 mL of THF, added dropwise to 500 mL of saturated NH$_3$ in THF and was allowed to stir overnight. The mixture was concentrated in vacuo to a crude yellow solid, the residue filtered through 50 g of silica gel using 70% ethyl acetate-hexanes as the eluent and the solution was then concentrated. The residue was recrystallized from the minimum amount of dichloromethane in hexanes with 1-2 drops of methanol to provide 2.49 g (41%) of cyclopentylsulfonamide as a white solid. $^1$H NMR (CDCl$_3$) δ 1.58-1.72 (m, 2H), 1.74-1.88 (m, 2H), 1.94-2.14 (m, 4H), 3.48-3.59 (m, 1H), 4.80 (br s, 2H); $^{13}$C NMR (CDCl$_3$) δ 25.90, 28.33, 63.54; MS m/e 148 (M-H)$^-$.

4c. Preparation of Cyclohexyl Sulfonamide

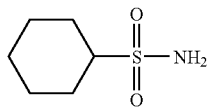

A solution of 18.5 mL (37.0 mmol) of 2M cyclohexylmagnesium chloride (TCI Americas) in diethyl ether was added dropwise to a solution of 3.0 mL (37.0 mmol) freshly distilled sulfuryl chloride in 100 mL of hexanes cooled to −78° C. The mixture was warmed to 0° C. over 1 hour and was then carefully concentrated in vacuo. This mixture was redissolved in diethyl ether (200 mL), washed once with some ice-cold water (200 mL), dried (MgSO$_4$), filtered, and concentrated carefully. This mixture was redissolved in 35 mL of THF, added dropwise to 500 mL of saturated NH$_3$ in THF and was allowed to stir overnight. The mixture was concentrated in vacuo to a crude yellow solid, the residue filtered through 50 g of silica gel using 70% ethyl acetate-hexanes as the eluent and was concentrated. The concentrate was recrystallized from the minimum amount of dichloromethane in hexanes with 1-2 drops of methanol to provide 1.66 g (30%) of cyclohexyl-sulfonamide as a white solid: $^1$H NMR (CDCl$_3$) δ 1.11-1.37 (m, 3H), 1.43-1.56 (m, 2H), 1.67-1.76 (m, 1H), 1.86-1.96 (m, 2H), 2.18-2.28 (m, 2H), 2.91 (tt, J=12, 3.5 Hz, 1H), 4.70 (br s, 2H); $^{13}$C NMR (CDCl$_3$) δ 25.04, 25.04, 26.56, 62.74; MS m/e 162 (M-1)$^-$.

4d. Preparation of Neopentylsulfonamide

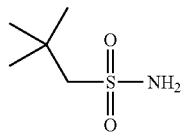

Following the procedure for the preparation of cyclohexylsulfonamide, 49 mL (37 mmol) of 0.75M neopentylmagnesium chloride (Alfa) in diethyl ether was converted to 1.52 g (27%) of neopentylsulfonamide as a white solid. $^1$H NMR (CDCl$_3$) δ 1.17 (s, 9H), 3.12 (s, 2H), 4.74 (brs, 2H); $^{13}$C NMR (CDCl$_3$) δ 29.46, 31.51, 67.38; MS m/e 150 (M-1)$^-$.

4e. Preparation of Cyclobutylcarbinylsulfonamide

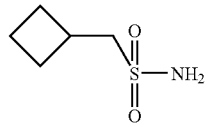

A solution of 12.3 g (83 mmol) of cyclobutylcarbinyl bromide (Aldrich) and 13.7 g (91 mmol) of sodium iodide in 150 mL of acetone was heated to reflux overnight and then cooled to room temperature. The inorganic solids were removed by filtration and the acetone and cyclopropylcarbinyl iodide (8.41 g, 46%) were removed by distillation (ambient temperature and 150 torr at 80° C., respectively).

A solution of 4.0 g (21.98 mmol) of cyclobutyl carbinyl iodide in 30 mL of anhydrous diethyl ether cooled to −78° C. was cannulated into a solution of 17 mL (21.98 mmol) of 1.3M sec-butyllithium in cyclohexanes and the solution was stirred for 5 minutes. To this mixture was cannulated a solution of 3.0 g (21.98 mmol) of freshly distilled sulfuryl chloride in 110 mL of hexanes cooled to −78° C., the mixture warmed to room temperature over 1 hour and was then carefully concentrated in vacuo. This mixture was redissolved in diethyl ether, washed once with some ice-cold water, dried (MgSO$_4$), filtered, and concentrated carefully. This mixture was redissolved in 30 mL of THF, added dropwise to 500 mL of saturated NH$_3$ in THF and was allowed to stir overnight. The mixture was concentrated in vacuo to a crude yellow solid and was recrystallized from the minimum amount of dichloromethane in hexanes with 1-2 drops of methanol to afford 1.39 g (42%) of cyclobutyl carbinylsulfonamide as a white solid. $^1$H NMR (CDCl$_3$) δ 1.81-2.03 (m, 4H), 2.14-2.28 (m, 2H), 2.81-2.92 (m, 1H), 3.22 (d, J=7 Hz, 2H), 4.74 (brs, 2H); $^{13}$C NMR (CDCl$_3$) δ 19.10, 28.21, 30.64, 60.93; MS m/e 148 (M-1)$^-$. time: 1.73, method B), 818 (M$^+$+H)

4f. Preparation of cyclopropylcarbinylsulfonamide

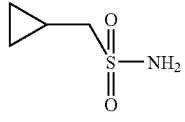

Using the procedure employed for the preparation of cyclobutylcarbinylsulfonamide, cyclopropylcarbinylsulfonamide was prepared from cyclopropylcarbinyl bromide (Aldrich) (see also *JACS* 1981, p. 442-445). $^1$H NMR (CDCl$_3$) δ 0.39-0.44 (m, 2H), 0.67-0.76 (m, 2H), 1.13-1.27 (m, 1H), 3.03 (d, J=7.3 Hz, 2H), 4.74 (brs, 2H); $^{13}$C NMR (CDCl$_3$) δ 4.33, 5.61, 59.93; MS m/e 134 (M−1).

4g. Preparation of 2-thiophenesulfonamide

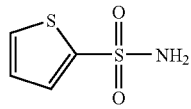

The desired product was prepared from 2-thiophenesulfonyl chloride (purchased from Aldrich) using the method described in *Justus Liebigs Ann. Chem.*, 501, 1933, p. 174-182.

4h. Preparation of 4-bromobenzenesulfonamide

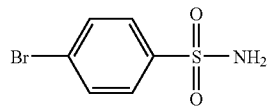

4-Bromophenylsulfonamide was prepared by treatment of commercially available 4-bromosulfonyl chloride with saturated ammonia in THF.

5. General Procedure for the Preparation of Sulfamides

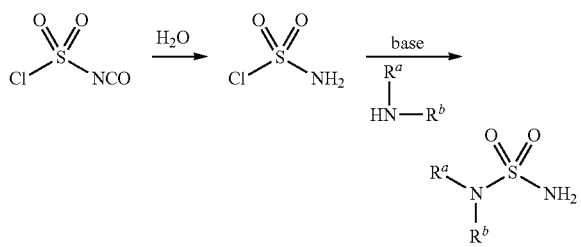

The intermediate sulfamoyl chloride was prepared by addition of water (1 equiv) in THF to a cold (−20° C.) stirred solution of chlorosulfonyl isocyanate (1 equiv) in THF and the resulting solution was allowed to warm to 0° C. To this solution was added anhydrous triethylamine (1 equiv) followed by requisite secondary amine (1 equiv). The reaction mixture was warmed to room temperature, then filtered and the filtrate was concentrated to afford the desired sulfamides.

III. Preparation of P1'-P1 Intermediates

1a. Preparation of cyclopropanesulfonic acid (1-(R)-amino-2-(S)-vinyl-cyclopropanecarbonyl)amide HCl salt

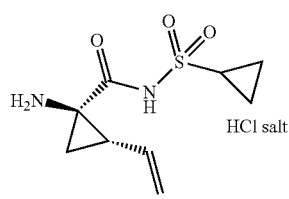

Step 1: Preparation of 1(R)-tert-butoxycarbonylamino-2(S)-vinyl-cyclopropanecarboxylic acid

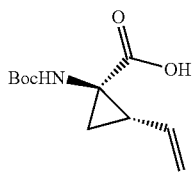

To a solution of 1(R)-tert-butoxycarbonylamino-2(S)-vinyl-cyclopropanecarboxylic acid ethyl ester (3.28 g, 13.2 mmol) in THF (7 mL) and methanol (7 mL) was added a suspension of LiOH (1.27 g, 53.0 mmol) in water (14 mL). The mixture was stirred overnight at room temperature and quenched with 1N NaOH (15 mL) and water (20 mL). The resulting mixture was washed with ethyl acetate (20 mL), and the organic phase was extracted with 20 mL 0.5N NaOH. The combined aqueous phases were acidified with 1N HCl to pH 4 and extracted with ethyl acetate (3×40 mL). The combined organic extracts were washed with brine, dried (MgSO$_4$), filtered and concentrated to provide the desired compound as a white solid (2.62 g, 87%). $^1$HNMR: (DMSO-d$_6$) δ 1.22-1.26 (m, 1H), 1.37 (s, 9H), 1.50-1.52 (m, 1H), 2.05 (q, J=9 Hz, 1H), 5.04 (d, J=10 Hz, 1H), 5.22 (d, J=17 Hz, 1H), 5.64-5.71 (m, 1H), 7.18, 7.53 (s, NH (rotamers), 12.4 (br s, 1H)); LC-MS (retention time: 1.67 minutes, method B), MS m/z 228 (M$^+$+H).

Step 2: Preparation of cyclopropanesulfonic acid (1-(R)-tert-butoxycarbonylamino-2-(S)-vinylcyclopropanecarbonyl)amide

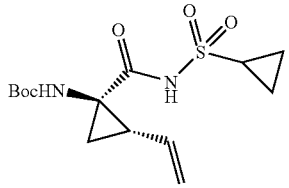

A solution of the product of Step 1 (2.62 g, 11.5 mmol) and CDI (2.43 g, 15.0 mmol) in THF (40 mL) was heated to reflux for 50 minutes under nitrogen. The solution was cooled to room temperature and transferred by cannula to a solution of cyclopropylsulfonamide (1.82 g, 15.0 mmol) in THF (10 mL). To the resulting solution was added DBU (2.40 mL, 16.1 mmol) and stirring was continued for 20 hours. The mixture was quenched with 1N HCl to pH 1 and THF was concentrated in vacuo. The suspension was extracted with ethyl acetate (2×50 mL) and the combined organic extracts were dried (Na$_2$SO$_4$), filtered, and concentrated. Purification by recrystallization from hexanes-ethyl acetate (1:1) provided the desired product (2.4 g) as a white solid. The mother liquor was purified by a Biotage 40S column (eluted 9% acetone in dichloromethane) to give a second batch of the desired product (1.1 g). Both batches were combined (total yield 92%). $^1$H NMR (DMSO-d$_6$) δ 0.96-1.10 (m, 4H), 1.22 (dd, J=5.5, 9.5 Hz, 1H), 1.39 (s, 9H), 1.70 (t, J=5.5 Hz, 1H), 2.19-2.24 (m, 1H), 2.90 (m, 1H), 5.08 (d, J=10 Hz, 1H), 5.23 (d, J=17 Hz, 1H), 5.45 (m, 1H), 6.85, 7.22 (s, NH (rotamers); LC-MS (retention time: 1.70 minutes, method B), MS m/z 331 (M$^+$+H).

Step 3: Preparation of cyclopropanesulfonic acid (1-(R)-amino-2-(S)-vinyl-cyclopropanecarbonyl) amide HCl salt

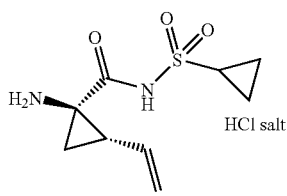

A solution of the product of Step 2 (3.5 g, 10.6 mmol) in dichloromethane (35 mL) and TFA (32 mL) was stirred at room temperature for 1.5 hours. The volatiles were removed in vacuo and the residue was suspended in 1N HCl in diethyl ether (20 mL) and concentrated in vacuo. This procedure was repeated once. The resulting mixture was triturated from pentane and filtered to provide the desired product as a hygroscopic, off-white solid (2.60 g, 92%). $^1$H NMR: (DMSO-d$_6$) δ 1.01-1.15 (m, 4H), 1.69-1.73 (m, 1H), 1.99-2.02 (m, 1H), 2.38 (q, J=9 Hz, 1H), 2.92-2.97 (m, 1H), 5.20 (d, J=11 Hz, 1H), 5.33 (d, J=17 Hz, 1H), 5.52-5.59 (m, 1H), 9.17 (br s, 3H) LC-MS (retention time: 0.24 minutes, method B), MS m/z 231 (M$^+$+H).

1b. Preparation of P1-P1' Sulfamide Derivative

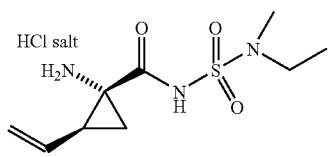

To a solution of (1R,2S) 1-tert-butoxycarbonylamino-2-vinyl-cyclopropanecarboxylic acid (217 mg, 1.194 mmol) in THF (5 mL), was added CDI (290 mg, 1.791 mmol) and the reaction mixture was heated to reflux for 45 minutes. In another round-bottomed flask, LiHMDS (1.0M solution in hexanes, 2.4 mL, 2.4 mmol) was added to a solution of N-ethylmethylsulfamide (330 mg, 2.388 mmol) in THF (5 mL) and the reaction mixture was stirred at room temperature for 1 hour. The two reaction mixtures were combined and stirred at room temperature for 2 hours. Water was added to quench the reaction and the reaction solution was extracted with ethyl acetate. The organic layer was separated and dried over MgSO$_4$. Filtration and concentration gave crude product which was purified by preparative HPLC to afford the desired N-Boc protected N-acylsulfamide. The Boc protecting group was then removed as the compound was dissolved in 4N HCl solution in dioxane (2 mL) and stirred at room temperature for 4 hours. Concentration provided a brownish oil as the HCl salt. (112 mg, 33% yield). $^1$H NMR (400 Mz, CD$_3$OD) δ 1.16 (t, J=7.21 Hz, 3H), 1.68 (dd, J=10.03, 7.83 Hz, 1H), 2.15 (m, 1H), 2.37 (m, 1H), 2.89 (s, 3H), 3.30 (m, 2H), 5.31 (d, J=10.27 Hz, 1H), 5.42 (d, J=17.12 Hz, 3H), 5.68 (m, 1H). LC-MS (retention time: 0.883 minutes), MS m/z 270 (M+Na$^+$).

Section B: Preparation of Compounds of the Disclosure

Preparation of Compound 1

Compound 1

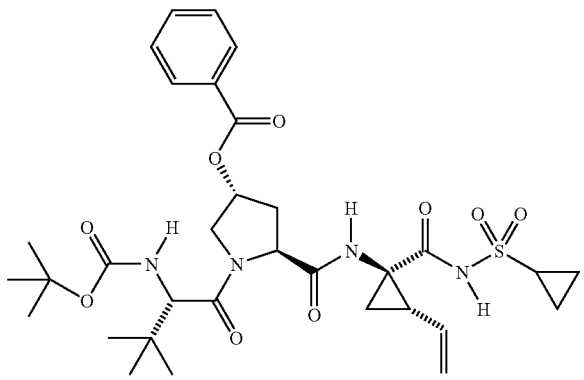

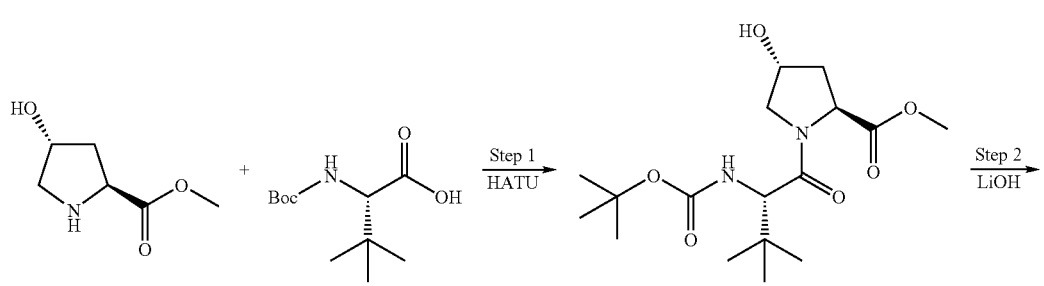

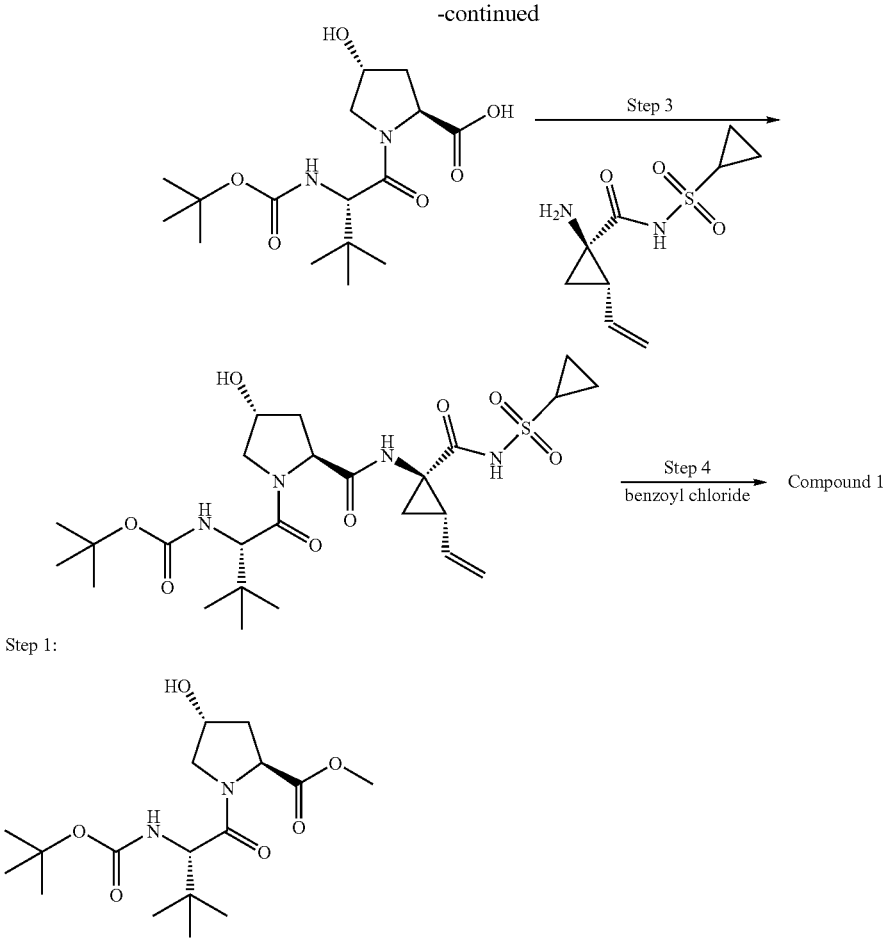

Step 1:

To a slurry of (2S,4R)-methyl 4-hydroxypyrrolidine-2-carboxylate HCl salt (5.45 g, 30.0 mmol), (S)-2-(tert-butoxycarbonyl)-3,3-dimethylbutanoic acid (6.93 g, 30.0 mmol), and HATU (17.1 g, 45.0 mmol) in dichloromethane (100 mL) at 0° C. was added diisopropylethylamine (16.8 g, 150 mmol) dropwise. The formed solution was stirred at room temperature overnight, washed with iced 5% citric acid and 1M NaOH (aq) twice, and then with brine, dried over MgSO$_4$, and filtered. The filtrate was concentrated in vacuo to provide 10.75 g (100%) as light brownish foam. $^1$H NMR (CD$_3$OD) δ 1.04 (s, 9H), 1.46 (s, 9H), 2.01-2.06 (m, 1H), 2.27-2.29 (m, 1H), 3.73 (s, 3H), 3.77-3.87 (m, 2H), 4.31 (s, 1H), 4.49 (br, 1H), 4.56 (t, J=8.5 Hz, 1H).

Step 2

To a solution of the product of Step 1 (10.75 g, 30.0 mmol) in THF (100 mL) and methanol (100 mL) was added LiOH monohydrate (6.30 g, 150 mmol) solution in water (100 mL). The resulting solution was stirred at room temperature overnight and concentrated in vacuo. The residue was acidified with 1M HCl to pH 2, extracted with ethyl acetate (100 mL), washed with 5% citric acid, and brine, dried over MgSO$_4$, and filtered. The filtrate was concentrated in vacuo to provide 8.95 g (87%) of the desired product as off-white foam. $^1$H NMR (CD$_3$OD) δ 1.05 (s, 9H), 1.45 (s, 9H), 2.03-2.06 (m, 1H), 2.32-2.36 (m, 1H), 3.79-3.86 (m, 2H), 4.32 (br, 1H), 4.49 (br, 1H), 4.54 (t, J=8.5 Hz, 1H).

Step 3

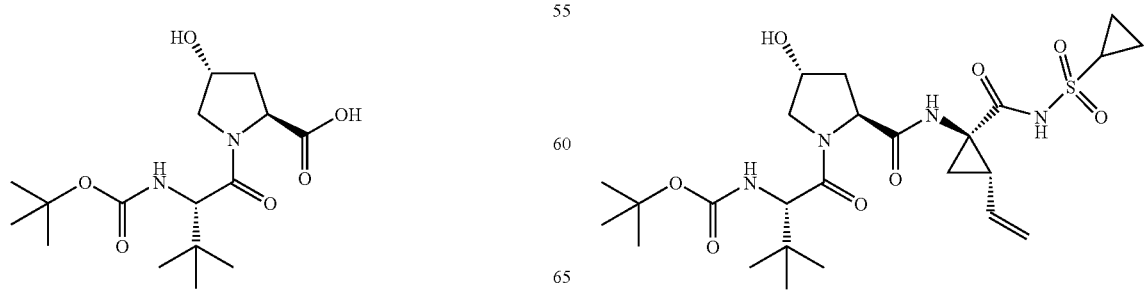

To a solution of the product from Step 2 (1.95 g, 5.68 mmol) in ethyl acetate (150 mL) at 0° C. was added (1R,2S)-1-amino-N-(cyclopropylsulfonyl)-2-vinylcyclopropanecarboxamide HCl salt (1.51 g, 5.68 mmol). The mixture was stirred at this temperature for 5 minutes before the dropwise addition of diisopropylethylamine (1.91 g, 17.0 mmol). The resulting clear solution was stirred at 0° C. for another 5 minutes before the addition of EDC (1.41 g, 7.38 mmol) and HOBt (0.77 g, 5.68 mmol). The resulting slurry was stirred at room temperature overnight and formed a clear solution which was washed with iced 5% citric acid twice, saturated sodium citrate (aq) and brine respectively, dried over MgSO$_4$, and filtered. The filtrate was concentrated in vacuo, purified by flash column chromatography eluting with 1:1 hexane-acetone to yield 2.50 g (79%) of the desired product as white foam. $^1$H NMR (CD$_3$OD) δ 1.00-1.10 (m, 11H), 1.24-1.28 (m, 2H), 1.41-1.46 (m, 10H), 1.86-1.91 (m, 1H), 2.00-2.04 (m, 1H), 2.12-2.28 (m, 1H), 2.92-2.99 (m, 1H), 3.80-3.95 (m, 2H), 4.30-4.40 (m, 2H), 4.51 (br, 1H), 5.14 (d, J=12 Hz, 1H), 5.35 (d, J=18.5 Hz, 1H), 5.77-5.82 (m, 1H); LC-MS (retention time: 2.40 minutes, method B), MS m/z 557 (M$^+$+H).

Step 4

To a solution of DMAP (24 mg), triethylamine (40 mg), and the product of Example 73, Step 3 (111 mg) in dichloromethane (50 mL) was added 4-benzoyl chloride (28 mg). The solution was stirred at room temperature for 4 hours and concentrated in vacuo. The residue was triturated by preparative HPLC to yield 95 mg (72%) of Compound 1 as a white solid. $^1$H NMR (CD$_3$OD) δ 1.07 (m, 11H), 1.25 (m, 11H), 1.43 (dd, J=9.44, 5.41 Hz, 1H), 1.87 (dd, J=8.18, 5.41 Hz, 1H), 2.24 (m, 2H), 2.49 (m, 1H), 2.94 (m, 1H), 4.01 (m, 1H), 4.23 (m, 1H), 4.34 (m, 1H), 4.46 (dd, J=10.32, 7.05 Hz, 1H), 5.12 (d, J=10.32 Hz, 1H), 5.29 (d, J=17.12 Hz, 1H), 5.61 (s, 1H), 5.75 (m, 1H), 7.44 (t, J=7.68 Hz, 2H), 7.60 (t, J=7.43 Hz, 1H), 8.01 (d, J=8.4 Hz, 2H); MS m/z 683 (M+Na)$^+$.

Preparation of Compound 2

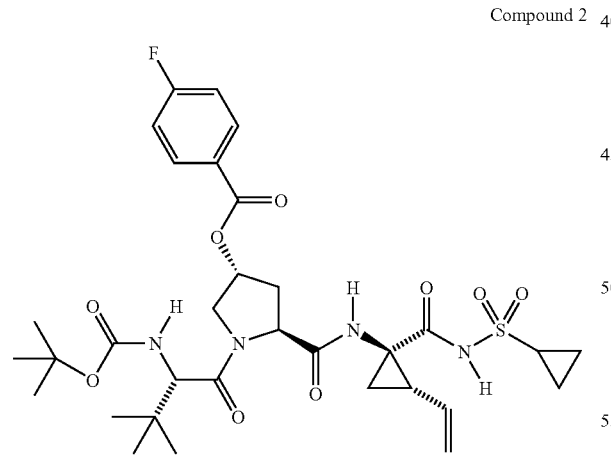

Compound 2

Compound 2 was prepared by the same procedure as described in the preparation of Compound 1, Step 4 using 4-fluorobenzoyl chloride. $^1$H NMR (400 MHz, CD$_3$OD) δ 1.06 (m, 11H), 1.25 (m, 11H), 1.43 (dd, J=9.44, 5.41 Hz, 1H), 1.87 (dd, J=8.18, 5.41 Hz, 1H), 2.23 (m, 2H), 2.48 (dd, J=13.72, 6.92 Hz, 1H), 2.93 (m, 1H), 3.99 (d, J=8.06 Hz, 1H), 4.21 (m, 1H), 4.35 (d, J=12.09 Hz, 1H), 4.46 (m, 1H), 5.12 (dd, J=10.32, 1.51 Hz, 1H), 5.30 (d, J=17.12 Hz, 1H), 5.60 (s, 1H), 5.75 (m, 1H), 7.17 (t, J=8.56 Hz, 2H), 8.07 (m, 2H); MS m/z 701 (M+Na)$^+$.

Preparation of Compound 3

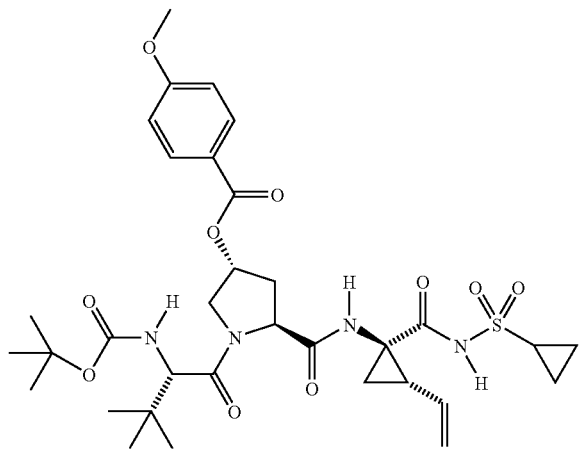

Compound 3

Compound 3 was prepared by the same procedure as described in the preparation of Compound 1, Step 4, using 4-methoxybenzoyl chloride. $^1$H NMR (400 MHz, CD$_3$OD) δ 1.06 (m, 11H), 1.25 (m, 11H), 1.43 (m, 1H), 1.87 (dd, J=8.18, 5.41 Hz, 1H), 2.24 (m, 2H), 2.47 (m, 1H), 2.94 (m, 1H), 3.85 (s, 3H), 3.99 (d, J=12.34 Hz, 1H), 4.27 (m, 2H), 4.45 (m, 1H), 5.12 (d, J=10.58 Hz, 1H), 5.30 (d, J=17.37 Hz, 1H), 5.57 (s, 1H), 5.75 (m, 1H), 6.95 (d, J=8.31 Hz, 2H), 7.96 (d, J=9.06 Hz, 2H); MS m/z 713 (M+Na)$^+$.

Preparation of Compound 4

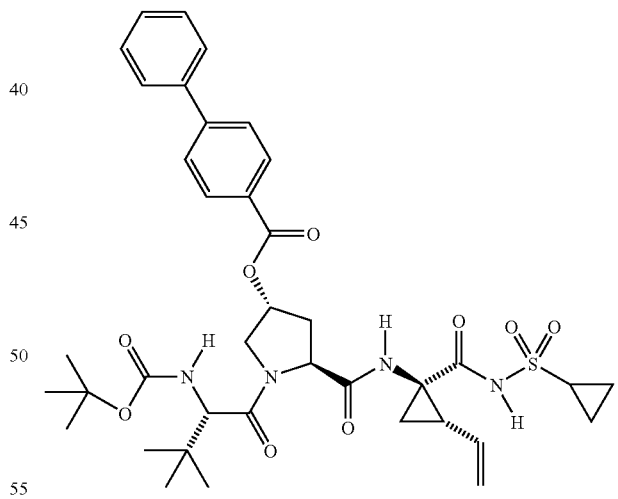

Compound 4

Compound 4 was prepared by the same procedure as described in the preparation of Compound 1, Step 4 using 4-phenylbenzoyl chloride. $^1$H NMR (400 MHz, CD$_3$OD) δ 1.05 (m, 11H), 1.24 (m, 11H), 1.44 (dd, J=9.32, 5.29 Hz, 1H), 1.88 (dd, J=8.31, 5.54 Hz, 1H), 2.25 (m, 2H), 2.51 (dd, J=14.23, 6.92 Hz, 1H), 2.94 (m, 1H), 4.01 (m, 1H), 4.25 (m, 1H), 4.38 (d, J=12.34 Hz, 1H), 4.49 (dd, J=10.20, 7.18 Hz, 1H), 5.13 (dd, J=10.32, 1.51 Hz, 1H), 5.30 (d, J=17.12 Hz, 1H), 5.63 (s, 1H), 5.75 (m, 1H), 7.42 (m, 3H), 7.67 (m, J=22.54, 7.93 Hz, 4H), 8.08 (d, J=8.56 Hz, 2H); MS m/z 759 (M+Na)$^+$.

Preparation of Compound 5

Compound 5

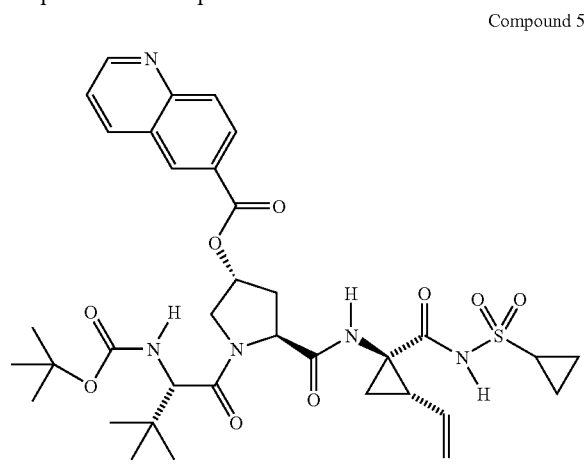

Compound 5 was prepared by the same procedure as described in the preparation of Compound 1, Step 4, using quinoline-6-carbonyl chloride hydrochloride. $^1$H NMR (400 MHz, CD$_3$OD) δ 1.01 (m, 11H), 1.23 (m, 11H), 1.45 (dd, J=9.44, 5.41 Hz, 1H), 1.89 (dd, J=7.93, 5.41 Hz, 1H), 2.23 (m, 2H), 2.56 (dd, J=14.10, 6.80 Hz, 1H), 2.94 (m, 1H), 4.03 (d, J=14.86 Hz, 1H), 4.22 (d, J=9.32 Hz, 1H), 4.43 (d, J=11.83 Hz, 1H), 4.54 (m, 1H), 5.13 (d, J=10.32 Hz, 1H), 5.30 (d, J=16.87 Hz, 1H), 5.72 (m, 2H), 7.63 (dd, J=8.18, 4.41 Hz, 1H), 8.08 (d, J=8.81 Hz, 1H), 8.31 (m, 1H), 8.49 (d, J=7.81 Hz, 1H), 8.67 (d, J=1.51 Hz, 1H), 8.97 (dd, J=4.28, 1.51 Hz, 1H); MS m/z 713 (M+Na)$^+$.

The following compounds were prepared following the Schemes and Examples shown above:

Compound 6

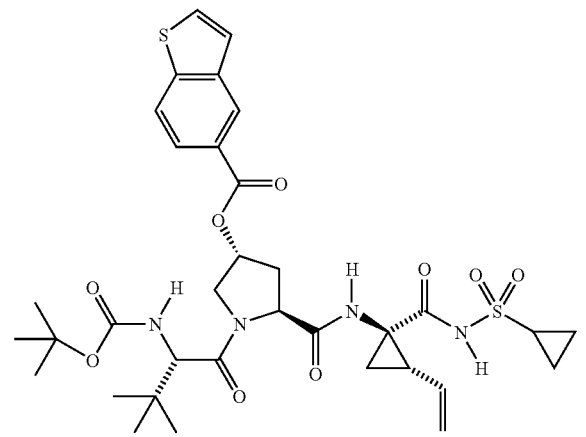

Compound 7

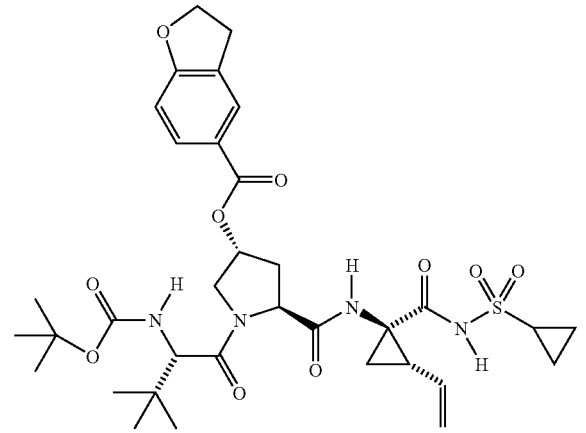

Biological Studies

HCV NS3/4A protease complex enzyme assays and cell-based HCV replicon assays were utilized in the present disclosure, and were prepared, conducted and validated as follows:

Generation of Recombinant HCV NS3/4A Protease Complex

HCV NS3 protease complexes, derived from the BMS strain, H77 strain or J4L6S strain, were generated, as described below. These purified recombinant proteins were generated for use in a homogeneous assay (see below) to provide an indication of how effective compounds of the present disclosure would be in inhibiting HCV NS3 proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR(RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, J. Clin. Microbiol., 31(6), 1493-1503 (1993)). The amino acid sequence of the nonstructural region, NS2-5B, was shown to be 97% identical to HCV genotype 1a (H77) and 87% identical to genotype 1b (J4L6S). The infectious clones, H77 (1a genotype) and J4L6S (1b genotype) were obtained from R. Purcell (NIH) and the sequences are published in Genbank (AAB67036, see Yanagi, M., Purcell, R. H., Emerson, S. U. and Bukh, J. Proc. Natl. Acad. Sci. U.S.A. 94(16), 8738-8743 (1997); AF054247, see Yanagi, M., St Claire, M., Shapiro, M., Emerson, S. U., Purcell, R. H. and Bukh, J, Virology 244 (1), 161-172. (1998)).

The H77 and J4L6S strains were used for production of recombinant NS3/4A protease complexes. DNA encoding the recombinant HCV NS3/4A protease complex (amino acids 1027 to 1711) for these strains was manipulated as described by P. Gallinari et al. (see Gallinari P, Paolini C, Brennan D, Nardi C, Steinkuhler C, De Francesco R. Biochemistry. 38(17):5620-32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in *Escherichia coli* strain BL21 (DE3) (Invitrogen) following the protocol described by P. Gallinari et al. (see Gallinari P, Brennan D, Nardi C, Brunetti M, Tomei L, Steinkuhler C, De Francesco R., J. Virol. 72(8):6758-69 (1998)) with modifications. Briefly, the NS3/4A protease complex expression was induced with 0.5 millimolar (mM) Isopropyl β-D-1-thiogalactopyranoside (IPTG) for 22 hours (h) at 20° C. A typical fermentation (1 Liter (L)) yielded approximately 10 grams (g) of wet cell paste. The cells were resuspended in lysis buffer (10 mL/g) consisting of 25 mM N-(2-Hydroxyethyl)piperazine-N'-(2-Ethane Sulfonic acid) (HEPES), pH 7.5, 20% glycerol, 500 mM Sodium Chloride (NaCl), 0.5% Triton X-100, 1 microgram/milliliter ("μg/mL") lysozyme, 5 mM Magnesium Chloride ($MgCl_2$), 1 μg/ml DnaseI, 5 mM β-Mercaptoethanol (βME), Protease inhibitor-Ethylenediamine Tetraacetic acid (EDTA) free (Roche), homogenized and incubated for 20 minutes (min) at 4° C. The homogenate was sonicated and clarified by ultra-centrifugation at 235000 g for 1 h at 4° C. Imidazole was added to the supernatant to a final concentration of 15 mM and the pH adjusted to 8.0. The crude protein extract was loaded on a Nickel-Nitrilotriacetic acid (Ni-NTA) column pre-equilibrated with buffer B (25 mM HEPES, pH 8.0, 20% glycerol, 500 mM NaCl, 0.5% Triton X-100, 15 mM imidazole, 5 mM βME). The sample was loaded at a flow rate of 1 mL/min. The column was washed with 15 column volumes of buffer C (same as buffer B except with 0.2% Triton X-100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH 7.5, 20% glycerol, 300 mM NaCl, 0.2% Triton X-100, 10 mM βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77 and J4L6S strains, were judged to be greater than 90% by SDS-PAGE and mass spectrometry analyses. The enzyme was stored at −80° C., thawed on ice and diluted prior to use in assay buffer.

FRET Peptide Assay to Monitor HCV NS3/4A Proteolytic Activity

The purpose of this in vitro assay was to measure the inhibition of HCV NS3 protease complexes, derived from the BMS strain, H77 strain or J4L6S strain, as described above, by compounds of the present disclosure. This assay provides an indication of how effective compounds of the present disclosure would be in inhibiting HCV NS3 proteolytic activity.

In order to monitor HCV NS3/4A protease activity, an NS3/4A peptide substrate was used. The substrate was RET S1 (Resonance Energy Transfer Depsipeptide Substrate; AnaSpec, Inc. cat #22991)(FRET peptide), described by Taliani et al. in Anal. Biochem. 240(2):60-67 (1996). The sequence of this peptide is loosely based on the NS4A/NS4B natural cleavage site for the HCV NS3 protease except there is an ester linkage rather than an amide bond at the cleavage site. The peptide also contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The peptide substrate was incubated with one of the three recombinant NS3/4A protease complexes, in the absence or presence of a compound of the present disclosure. The inhibitory effects of a compound were determined by monitoring the formation of fluorescent reaction product in real time using a Cytofluor Series 4000.

The reagents were as follow: HEPES and Glycerol (Ultra-pure) were obtained from GIBCO-BRL. Dimethyl Sulfoxide (DMSO) was obtained from Sigma. β-Mercaptoethanol was obtained from Bio Rad.

Assay buffer: 50 mM HEPES, pH 7.5; 0.15 M NaCl; 0.1% Triton; 15% Glycerol; 10 mM βME. Substrate: 2 μM final concentration (from a 2 mM stock solution in DMSO stored at −20° C.). HCV NS3/4A protease type 1a (1b), 2-3 nM final concentration (from a 5 μM stock solution in 25 mM HEPES, pH 7.5, 20% glycerol, 300 mM NaCl, 0.2% Triton-X100, 10 mM βME). For compounds with potencies approaching the assay limit, the assay was made more sensitive by adding 50 μg/ml Bovine Serum Albumin (Sigma) and 1 mM DTT to the assay buffer and reducing the end protease concentration to approximately 90 μM.

The assay was performed in a 96-well polystyrene black plate from Falcon. Each well contained 25 μl NS3/4A protease complex in assay buffer, 50 μl of a compound of the present disclosure in 10% DMSO/assay buffer and 25 μl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 min.

The percent inhibition was calculated with the following equation:

$$100-[(\delta F_{inh}/\delta F_{con}) \times 100]$$

where δF is the change in fluorescence over the linear range of the curve. A non-linear curve fit was applied to the inhibition-concentration data, and the 50% effective concentration ($IC_{50}$) was calculated by the use of Excel XLfit software using the equation, $y=A+((B-A)/(1+((C/x)^{\wedge}D)))$.

All of the compounds tested were found to inhibit the activity of the NS3/4A protease complex with IC50's of 13 nM or less. Further, compounds of the present disclosure, which were tested against more than one type of NS3/4A complex, were found to have similar inhibitory properties though the compounds uniformly demonstrated greater potency against the 1b strains as compared to the 1a strains.

Specificity Assays

The specificity assays were performed to demonstrate the in vitro selectivity of the compounds of the present disclosure in inhibiting HCV NS3/4A protease complex as compared to other serine or cysteine proteases.

The specificities of compounds of the present disclosure were determined against a variety of serine proteases: human neutrophil elastase (HNE), porcine pancreatic elastase (PPE) and human pancreatic chymotrypsin and one cysteine protease: human liver cathepsin B. In all cases a 96-well plate format protocol using colorimetric p-nitroaniline (pNA) substrate specific for each enzyme was used as described previously (PCT Patent Application No. WO 00/09543) with some modifications to the serine protease assays. All enzymes were purchased from Sigma while the substrates were from Bachem.

Each assay included a 2 h enzyme-inhibitor pre-incubation at room temperature followed by addition of substrate and hydrolysis to ~30% conversion as measured on a Spectramax Pro microplate reader. Compound concentrations varied from 100 to 0.4 μM depending on their potency.

The final conditions for each assay were as follows: 50 mM Tris(hydroxymethyl)aminomethane hydrochloride (Tris-HCl) pH 8, 0.5 M Sodium Sulfate ($Na_2SO_4$), 50 mM NaCl, 0.1 mM EDTA, 3% DMSO, 0.01% Tween-20 with: 133 μM succ-AAA-pNA and 20 nM HNE or 8 nM PPE; 100 μM succ-AAPF-pNA and 250 μM Chymotrypsin.

100 mM NaHPO$_4$ (Sodium Hydrogen Phosphate) pH 6, 0.1 mM EDTA, 3% DMSO, 1 mM TCEP (Tris(2-carboxyethyl) phosphine hydrochloride), 0.01% Tween-20, 30 µM Z-FR-pNA and 5 nM Cathepsin B (enzyme stock activated in buffer containing 20 mM TCEP before use).

The percentage of inhibition was calculated using the formula:

$$[1-((UV_{inh}-UV_{blank})/(UV_{ctl}-UV_{blank}))] \times 100$$

A non-linear curve fit was applied to the inhibition-concentration data, and the 50% effective concentration (IC$_{50}$) was calculated by the use of Excel Xl-fit software.

Generation of HCV Replicon

An HCV replicon whole cell system was established as described by Lohmann V, Korner F, Koch J, Herian U, Theilmann L, Bartenschlager R., Science 285(5424): 110-3 (1999). This system enabled us to evaluate the effects of our HCV Protease compounds on HCV RNA replication. Briefly, using the HCV strain 1b sequence described in the Lohmann paper (Assession number: AJ238799), an HCV cDNA was synthesized by Operon Technologies, Inc. (Alameda, Calif.), and the full-length replicon was then assembled in plasmid pGem9zf(+) (Promega, Madison, Wis.) using standard molecular biology techniques. The replicon consists of (i) the HCV 5' UTR fused to the first 12 amino acids of the capsid protein, (ii) the neomycin phosphotransferase gene (neo), (iii) the IRES from encephalomyocarditis virus (EMCV), and (iv) HCV NS3 to NS5B genes and the HCV 3' UTR. Plasmid DNAs were linearized with ScaI and RNA transcripts were synthesized in vitro using the T7 MegaScript transcription kit (Ambion, Austin, Tex.) according to manufacturer's directions. In vitro transcripts of the cDNA were transfected into the human hepatoma cell line, HUH-7. Selection for cells constitutively expressing the HCV replicon was achieved in the presence of the selectable marker, neomycin (G418). Resulting cell lines were characterized for positive and negative strand RNA production and protein production over time.

HCV Replicon FRET Assay

The HCV replicon FRET assay was developed to monitor the inhibitory effects of compounds described in the disclosure on HCV viral replication. HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/ml G418 (Gibco-BRL). Cells were seeded the night before (1.5×10$^4$ cells/well) in 96-well tissue-culture sterile plates. Compound and no compound controls were prepared in DMEM containing 4% FCS, 1:100 Penicillin/Streptomycin (Gibco-BRL), 1:100 L-glutamine and 5% DMSO in the dilution plate (0.5% DMSO final concentration in the assay). Compound/DMSO mixes were added to the cells and incubated for 4 days at 37° C. After 4 days, cells were first assessed for cytotoxicity using alamar Blue (Trek Diagnotstic Systems) for a CC$_{50}$ reading. The toxicity of compound (CC$_{50}$) was determined by adding 1/10$^{th}$ volume of alamar Blue to the media incubating the cells. After 4 h, the fluorescence signal from each well was read, with an excitation wavelength at 530 nm and an emission wavelength of 580 nm, using the Cytofluor Series 4000 (Perspective Biosystems). Plates were then rinsed thoroughly with Phosphate-Buffered Saline (PBS) (3 times 150 µl). The cells were lysed with 25 µl of a lysis assay reagent containing an HCV protease substrate (5× cell Luciferase cell culture lysis reagent (Promega #E153A) diluted to 1× with distilled water, NaCl added to 150 mM final, the FRET peptide substrate (as described for the enzyme assay above) diluted to 10 µM final from a 2 mM stock in 100% DMSO. The plate was then placed into the Cytofluor 4000 instrument which had been set to 340 nm excitation/490 nm emission, automatic mode for 21 cycles and the plate read in a kinetic mode. EC$_{50}$ determinations were carried out as described for the IC$_{50}$ determinations.

HCV Replicon Luciferase Reporter Assay

As a secondary assay, EC$_{50}$ determinations from the replicon FRET assay were confirmed in a replicon luciferase reporter assay. Utilization of a replicon luciferase reporter assay was first described by Krieger et al (Krieger N, Lohmann V, and Bartenschlager R, J. Virol. 75(10):4614-4624 (2001)). The replicon construct described for our FRET assay was modified by inserting cDNA encoding a humanized form of the Renilla luciferase gene and a linker sequence fused directly to the 3'-end of the luciferase gene. This insert was introduced into the replicon construct using an AscI restriction site located in core, directly upstream of the neomycin marker gene. The adaptive mutation at position 1179 (serine to isoleucine) was also introduced (Blight K J, Kolykhalov, A A, Rice, C M, Science 290(5498):1972-1974). A stable cell line constitutively expressing this HCV replicon construct was generated as described above. The luciferase reporter assay was set up as described for the HCV replicon FRET assay with the following modifications. Following 4 days in a 37° C./5% CO$_2$ incubator, cells were analyzed for Renilla Luciferase activity using the Promega Dual-Glo Luciferase Assay System. Media (100 µl) was removed from each well containing cells. To the remaining 50 µl of media, 50 µl of Dual-Glo Luciferase Reagent was added, and plates rocked for 10 min to 2 h at room temperature. Dual-Glo Stop & Glo Reagent (50 µl) was then added to each well, and plates were rocked again for an additional 10 min to 2 h at room temperature. Plates were read on a Packard TopCount NXT using a luminescence program.

The percentage inhibition was calculated using the formula below:

$$\% \text{ control} = \frac{\text{average luciferase signal in experimental wells (+compound)}}{\text{average luciferase signal in DMSO control wells (-compound)}}$$

The values were graphed and analyzed using XLfit to obtain the EC$_{50}$ value.

Representative compounds of the disclosure were assessed in the HCV enzyme assays, HCV replicon cell assay and/or in several of the outlined specificity assays. For example, Compound 1 was found to have an IC$_{50}$ of 13 nanomolar (nM) against the NS3/4A BMS strain in the enzyme assay. Similar potency values were obtained with the published H77 (IC$_{50}$ of 6 nM) and J4L6S (IC$_{50}$ of 2.5 nM) strains. The EC$_{50}$ value in the replicon FRET assay was 484 nM and 51 nM in the replicon Luciferase assay.

In the specificity assays, the same compound was found to have the following activity: HLE>200 µM; PPE>200 µM; Chymotrypsin>200 µM; Cathepsin B>50 µM. These results indicate this family of compounds is highly specific for the NS3 protease and many of these members inhibit HCV (for compounds tested) replicon replication.

The compounds of the current disclosure were tested and found to have activities in the ranges as follow:

$IC_{50}$ Activity Range (NS3/4A BMS Strain): A is >0.5 µM; B is 0.1-0.5 µM; C is 50-100 nM; D is 1-50 nM.

$EC_{50}$ Activity Ranges (for compounds tested): A is >1 µM; B is 0.2-1 µM; C is 25-200 nM.

Note that by using the example number and the compound number shown in Table 2 the structures of compounds can be found herein.

In accordance with one embodiment of the present disclosure, the compounds have a biological activity ($EC_{50}$) of 1 µM or less, and in another embodiment, 0.25 µM or less.

TABLE 2

| Example Number | Compound Number | Activity Range (IC50) | Activity Range (EC50) |
|---|---|---|---|
| 1 | 1 | D | B |
| 2 | 2 | D | B |
| 3 | 3 | D | C |
| 4 | 4 | D | B |
| 5 | 5 | D | C |
| 6 | 6 | D | C |
| 7 | 7 | D | C |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (II)

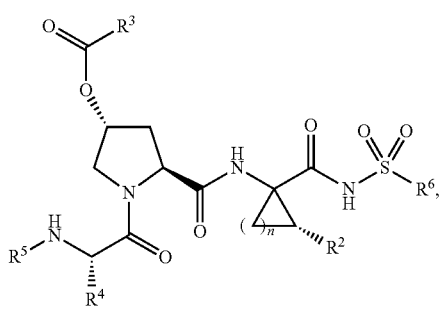

(II)

or a pharmaceutically acceptable salt thereof, wherein
n is 1, 2, or 3;
$R^2$ is selected from hydrogen, alkenyl, alkyl, and cycloalkyl, wherein the alkenyl, the alkyl, and the cycloalkyl are optionally substituted with one, two, or three substituents independently selected from alkoxy, carboxy, cyano, dialkylamino, and halo;
$R^3$ is selected from alkyl, haloalkyl, cyanoalkyl, alkenyl, aryl, arylalkyl, cycloalkyl, and (cycloalkyl)alkyl;
$R^4$ is selected from hydrogen, alkenyl, alkyl, and haloalkyl;
$R^5$ is selected from alkoxycarbonyl, alkylcarbonyl, ($NR^aR^b$)carbonyl, and ($NR^cR^d$)carbonyl;
$R^6$ is selected from alkyl, aryl, cycloalkyl, (cycloalkyl)alkyl, heterocyclyl, —$NR^aR^b$, and —$NR^cR^d$; wherein the cycloalkyl and the cycloalkyl part of the (cycloalkyl)alkyl can be optionally substituted with one substituent selected from alkoxy, alkyl, amino, cyano, halo, haloalkyl, and nitro;

$R^a$ and $R^b$ are independently selected from hydrogen and alkyl; and $R^c$ and $R^d$ together with the nitrogen atom to which they are attached form a five or six-membered monocyclic heterocyclic ring optionally containing one additional heteroatom selected from NH, O, and S.

2. The compound of claim 1 wherein n is 1 or 2; and $R^4$ is selected from hydrogen, alkenyl, and alkyl.

3. The compound of claim 1 wherein n is 1;

$R^2$ is alkenyl;

$R^4$ is alkyl; and $R^5$ is alkoxycarbonyl.

4. A compound of formula (III)

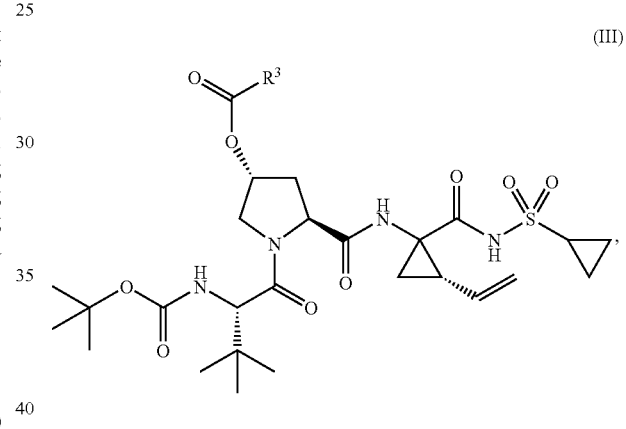

(III)

or a pharmaceutically acceptable salt thereof, wherein $R^3$ is selected from alkyl, haloalkyl, cyanoalkyl, alkenyl, aryl, arylalkyl, cycloalkyl, and (cycloalkyl)alkyl.

5. The compound of claim 4 wherein $R^3$ is aryl.

6. The compound of claim 5 wherein $R^3$ is selected from phenyl optionally substituted with one substituent selected from alkoxy, unsubstituted phenyl, and halo.

7. A compound selected from

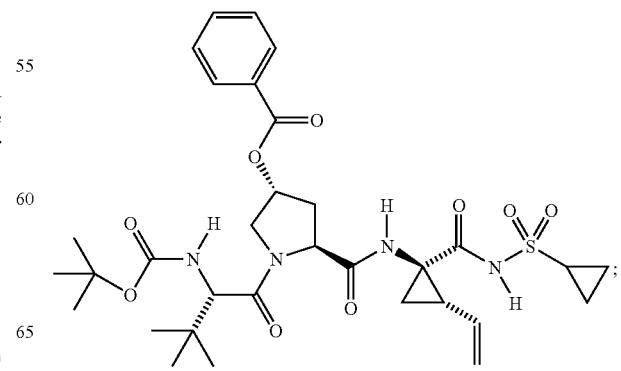

77
-continued

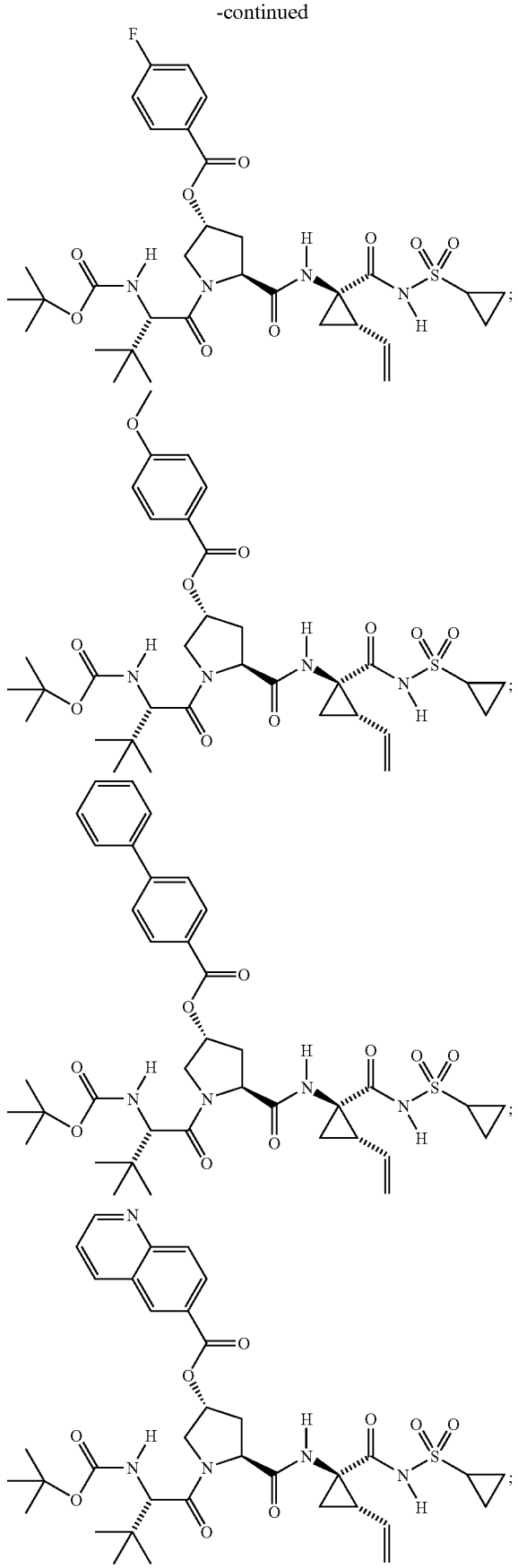

78
-continued

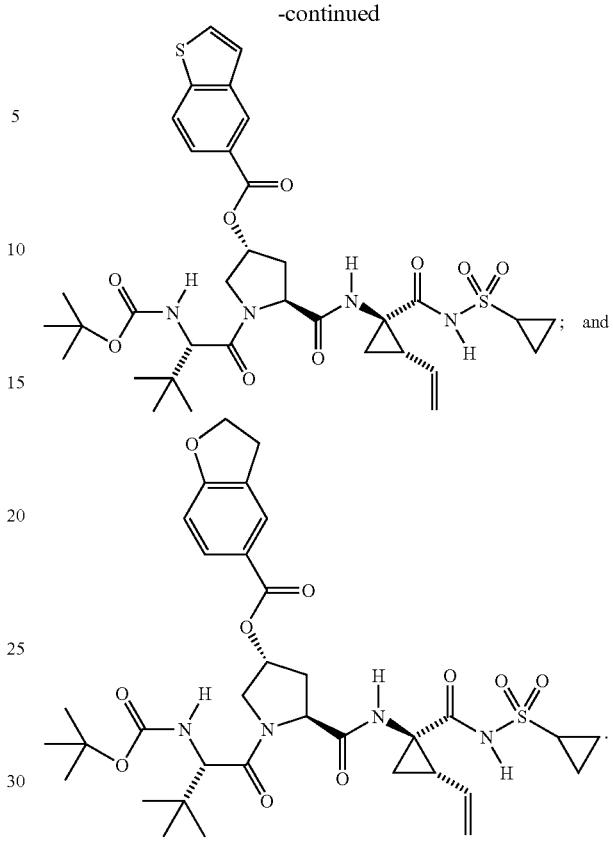

8. A composition comprising the compound of claim 1 and a pharmaceutically acceptable carrier.

9. The composition of claim 8 further comprising an interferon and ribavirin.

10. The composition of claim 8 further comprising a second compound having anti-HCV activity.

11. The composition of claim 10 wherein the second compound having anti-HCV activity is an interferon.

12. The composition of claim 11 wherein the interferon is selected from interferon alpha 2B, pegylated interferon alpha, consensus interferon, interferon alpha 2A, and lymphoblastiod interferon tau.

13. The composition of claim 10 wherein the second compound having anti-HCV activity is selected from interleukin 2, interleukin 6, interleukin 12, a compound that enhances the development of a type 1 helper T cell response, Imiqimod, ribavirin, an inosine 5'-monophospate dehycrogenase inhibitor, amantadine, and rimantadine.

14. A method of inhibiting the function of HCV serine protease comprising contacting the HCV serine protease with the compound of Formula (II) of claim 1.

15. A method of treating an HCV infection in a patient, comprising administering to the patient a therapeutically effective amount of the compound of Formula (II) of claim 1.

16. The method of claim 15 wherein the compound is effective to inhibit the function of the HCV serine protease.

17. The method of claim 15 further comprising administering a second compound having anti-HCV activity prior to, after, or simultaneously with the compound of Formula (II).

18. The method of claim 17 wherein the second compound having anti-HCV activity is an interferon.

19. The method of claim 18 wherein the interferon is selected from interferon alpha 2B, pegylated interferon alpha, consensus interferon, interferon alpha 2A, and lymphoblastiod interferon tau.

20. The method of claim 17 wherein the second compound having anti-HCV activity is selected from interleukin 2, interleukin 6, interleukin 12, a compound that enhances the development of a type 1 helper T cell response, Imiqimod, ribavirin, an inosine 5'-monophospate dehydrogenase inhibitor, amantadine, and rimantadine.

* * * * *

UNITED STATES PATENT AND TRADEMARK OFFICE
CERTIFICATE OF CORRECTION

| | | |
|---|---|---|
| PATENT NO. | : 7,935,670 B2 | Page 1 of 1 |
| APPLICATION NO. | : 11/775341 | |
| DATED | : May 3, 2011 | |
| INVENTOR(S) | : Paul Michael Scola et al. | |

It is certified that error appears in the above-identified patent and that said Letters Patent is hereby corrected as shown below:

In the Specification:

Column 6, line 19, change "lymphoblastiod" to -- lymphoblastoid --.

Column 6, line 27, change "Imiqimod" to -- Imiquimod --.

Column 6, line 27, change "5'-monophospate" to -- 5'-monophosphate --.

Column 6, lines 60 and 61, change "lymphoblastiod" to -- lymphoblastoid --.

Column 7, line 3, change "Imiqimod" to -- Imiquimod --.

Column 7, line 3, change "5'-monophospate" to -- 5'-monophosphate --.

In the Claims:

Claim 12:

Column 78, lines 45 and 46, change "lymphoblastiod" to -- lymphoblastoid --.

Claim 13:

Column 78, line 50, change "Imiqimod" to -- Imiquimod --.

Column 78, line 51, change "5'-monophospate dehycrogenase" to -- 5'-monophosphate dehydrogenase --.

Claim 19:

Column 79, lines 1 and 2, change "lymphoblastiod" to -- lymphoblastoid --.

Claim 20:

Column 80, line 1, change "Imiqimod" to -- Imiquimod --.

Column 80, line 2, change "5'-monophospate" to -- 5'-monophosphate --.

Signed and Sealed this

Twenty-seventh Day of December, 2011

David J. Kappos
*Director of the United States Patent and Trademark Office*